(12) United States Patent
Quinn

(10) Patent No.: US 8,906,672 B2
(45) Date of Patent: Dec. 9, 2014

(54) GRADIENT INJECTION FOR BIOSENSING

(75) Inventor: John Gerard Quinn, Edmond, OK (US)

(73) Assignee: Flir Systems, Inc., Wilsonville, OR (US)

( * ) Notice: Subject to any disclaimer, the term of this patent is extended or adjusted under 35 U.S.C. 154(b) by 1325 days.

(21) Appl. No.: 12/674,290

(22) PCT Filed: Jan. 16, 2008

(86) PCT No.: PCT/US2008/000547
§ 371 (c)(1),
(2), (4) Date: Aug. 22, 2011

(87) PCT Pub. No.: WO2009/025680
PCT Pub. Date: Feb. 26, 2009

(65) Prior Publication Data
US 2011/0295512 A1    Dec. 1, 2011

Related U.S. Application Data

(60) Provisional application No. 60/965,640, filed on Aug. 20, 2007.

(51) Int. Cl.
*C12M 1/34* (2006.01)
*G01N 35/10* (2006.01)
(Continued)

(52) U.S. Cl.
CPC .......... *G01N 35/1097* (2013.01); *G01N 21/553* (2013.01); *G01N 21/55* (2013.01);
(Continued)

(58) Field of Classification Search
CPC .............. G01N 21/553; G01N 21/554; G01N 21/7743; G01N 21/55; G01N 21/7703; G01N 21/01; G01N 21/658; G01N 33/54373; G01N 33/553; G01N 33/54306; G01N 33/6845; G01N 35/00693; G01N 35/1095; G01N 35/1097; G01N 35/08; G01N 35/085; B01L 2300/0636; B01L 2300/0867; B01L 3/5025; Y10S 436/806

USPC ......... 356/517, 481, 501; 422/68.1, 400, 502, 422/503, 82, 82.01, 82.05; 385/12, 129, 385/130; 435/7.1, 287.1, 287.2, 7.92, 435/283.1, 287.9, 288.2, 288.5; 436/518, 436/149, 151, 525, 806, 164, 517, 807
See application file for complete search history.

(56) References Cited

U.S. PATENT DOCUMENTS

2001/0027949 A1    10/2001  Safir et al.
(Continued)

FOREIGN PATENT DOCUMENTS

WO    WO 2004/109284 A1    12/2004
WO    WO 2004/109295 A1    12/2004

OTHER PUBLICATIONS

Frostell-Karlsson et al., Biosensor analysis of the interaction between immobilized human serum albumin and drug compounds for prediction of human serum albumin binding levels, 2000, Journal of Medicinal Chemistry, vol. 43, pp. 1986-1992.*

(Continued)

*Primary Examiner* — Melanie Y Brown
*Assistant Examiner* — Erik B Crawford
(74) *Attorney, Agent, or Firm* — McAfee & Taft

(57) ABSTRACT

A single injection gradient with a biosensor, both structural and methodological, achieves the binding of analyte to immobilized ligand over a wide concentration range without the necessity of regeneration of the sensing area. A gradient of concentrations adjacent to or within a flow cell facilitates kinetic analysis of interactions without requiring multiple discrete volumes or injections to achieve a range of concentrations. A continuous gradient fluid is preferably formed directly adjacent to the flow cell inlet or a region of sample/buffer dispersion at an injection point into a flow channel of a flow cell. The analyte gradient may be flowed through the flow cell from a low analyte concentration. Multiple component gradients are also provided.

3 Claims, 11 Drawing Sheets

(51) Int. Cl.
G01N 21/55 (2014.01)
G01N 33/53 (2006.01)
G01N 35/08 (2006.01)
G01N 21/05 (2006.01)

(52) U.S. Cl.
CPC ... B01L 2300/0636 (2013.01); G01N 2021/058 (2013.01); G01N 33/53 (2013.01); G01N 35/085 (2013.01); G01N 35/08 (2013.01); Y10S 435/808 (2013.01); Y10S 436/805 (2013.01)
USPC ...... 435/288.7; 422/68.1; 422/69; 422/82.11; 435/4; 435/7.1; 435/286.5; 435/287.1; 435/287.2; 435/287.9; 435/808; 436/52; 436/164; 436/501; 436/518; 436/805

(56) References Cited

U.S. PATENT DOCUMENTS

| 2002/0113095 | A1* | 8/2002 | Jeon et al. | 222/424.5 |
| 2003/0143565 | A1 | 7/2003 | Trutanau | |
| 2005/0019933 | A1* | 1/2005 | Andersson et al. | 436/52 |
| 2009/0040507 | A1* | 2/2009 | VanWiggeren | 356/73 |

OTHER PUBLICATIONS

Yijun Tang et al; Nonregeneration Protocol for Surface Plasmon Resonance: Study of High-Affinity Interaction with High-Density Biosensors; Anal. Chem. 2006, 78, 1841-1848.

Lars Nieba et al.; Competition BIAcore for Measuring True Affinities: Large Differences from Values Determined from Binding Kinetics; Analytical Biochemistry 234, 155-165 (1996) Article No. 0067.

Joydeep Lahiri et al.; A Strategy for the Generation of Surfaces Presenting Ligands for Studies of Binding Based on an Active Ester as a Common Reactive Intermediate: A Surface Plasmon Resonance Study; Anal. Chem. 1999, 71, 777-790.

Peter Schuck et al.; Determination of Binding Constants by Equilibrium Titration with Circulating Sample in a Surface Plasmon Resonance Biosensor; Analytical Biochemistry 265, 79-91 (1998) Article No. AB982872.

Harvey J. Motulsky et al.; The Kinetics of Competitive Radioligand Binding Predicted by the Law of Mass Action; Molecular Pharmacology, 25:1-9 1983.

Robert Karlsson; Real-Time Competitive Kinetic Analysis of Interactions between Low-Molecular-Weight Ligands in Solution and Surface-Immobilized Receptors; Analytical Biochemistry 221, 142-151 (1994).

Robert Karlsson; Affinity analysis of non-steady-state data obtained under mass transport limited conditions using BIAcore technology; J. Mol. Recognit. 1999;12:285-292.

Mary L. Shank-Retzlaff; Analyte Gradient-Surface Plasmon Resonance: A One-Step Method for Determining Kinetic Rates and Macromolecular Binding Affinities; Anal. Chem. 2000, 72, 4212-4220.

* cited by examiner

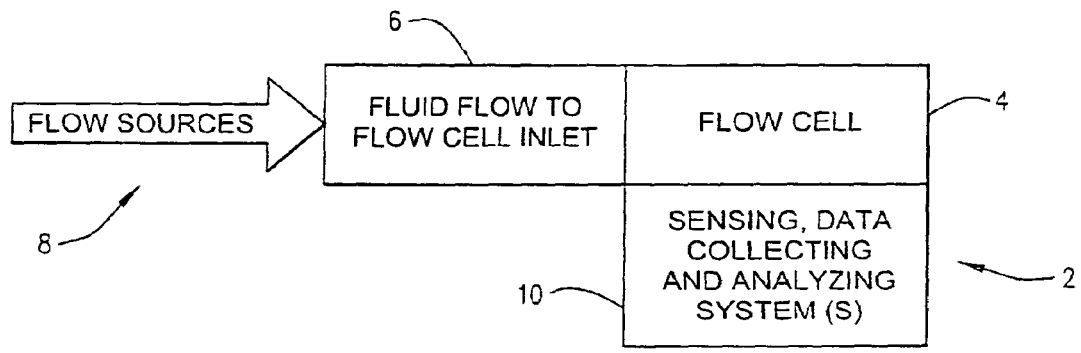
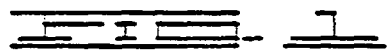
FIG. 1
PRIOR ART
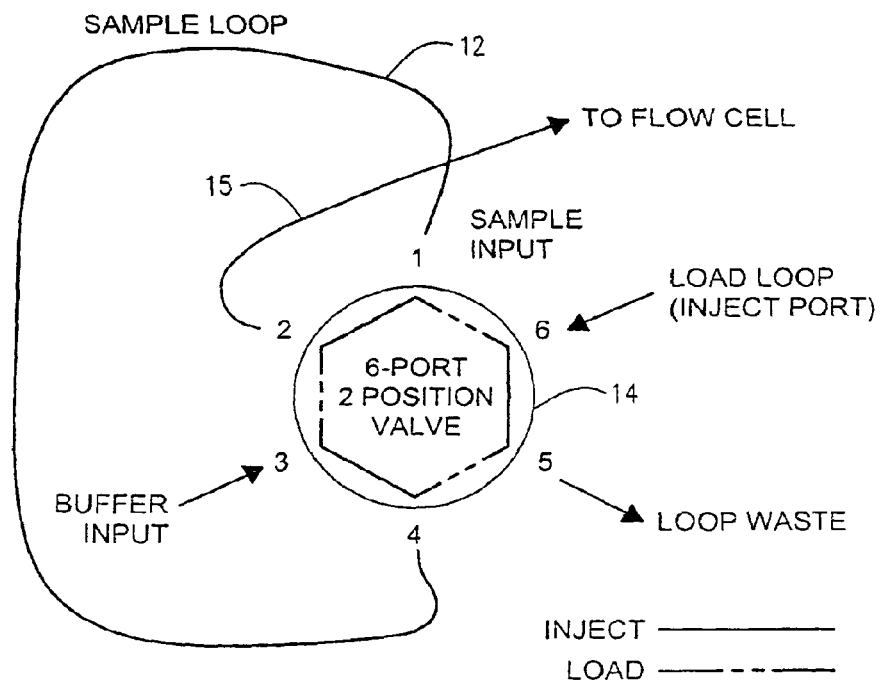
FIG. 2A
PRIOR ART

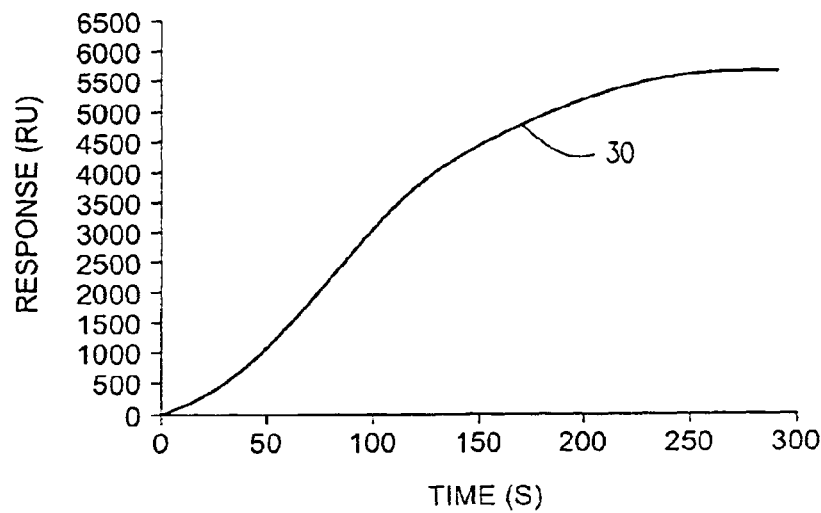
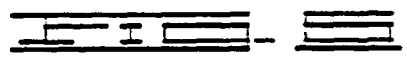
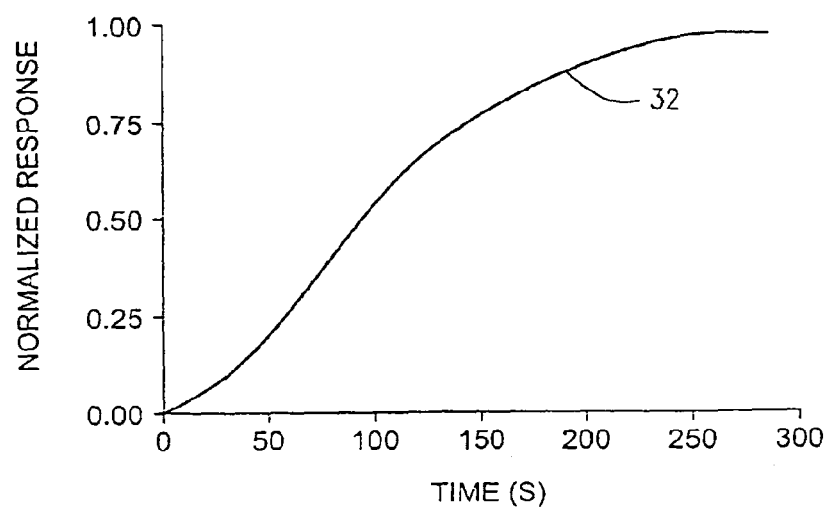
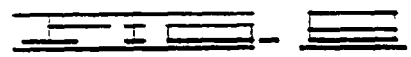

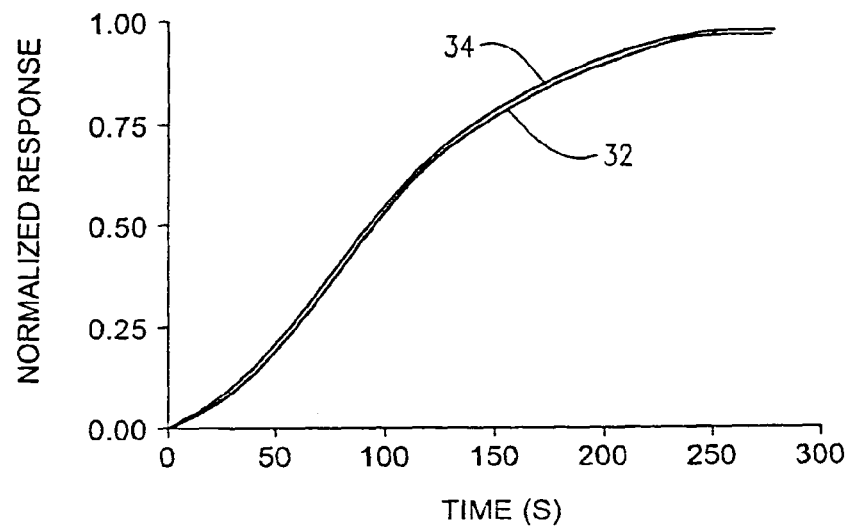
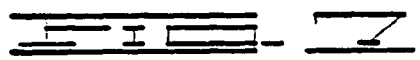
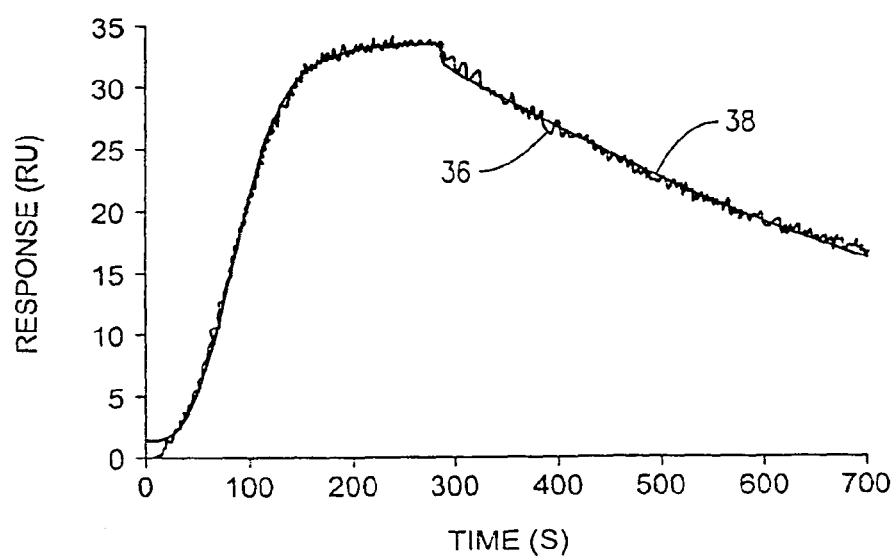
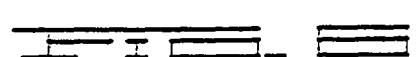

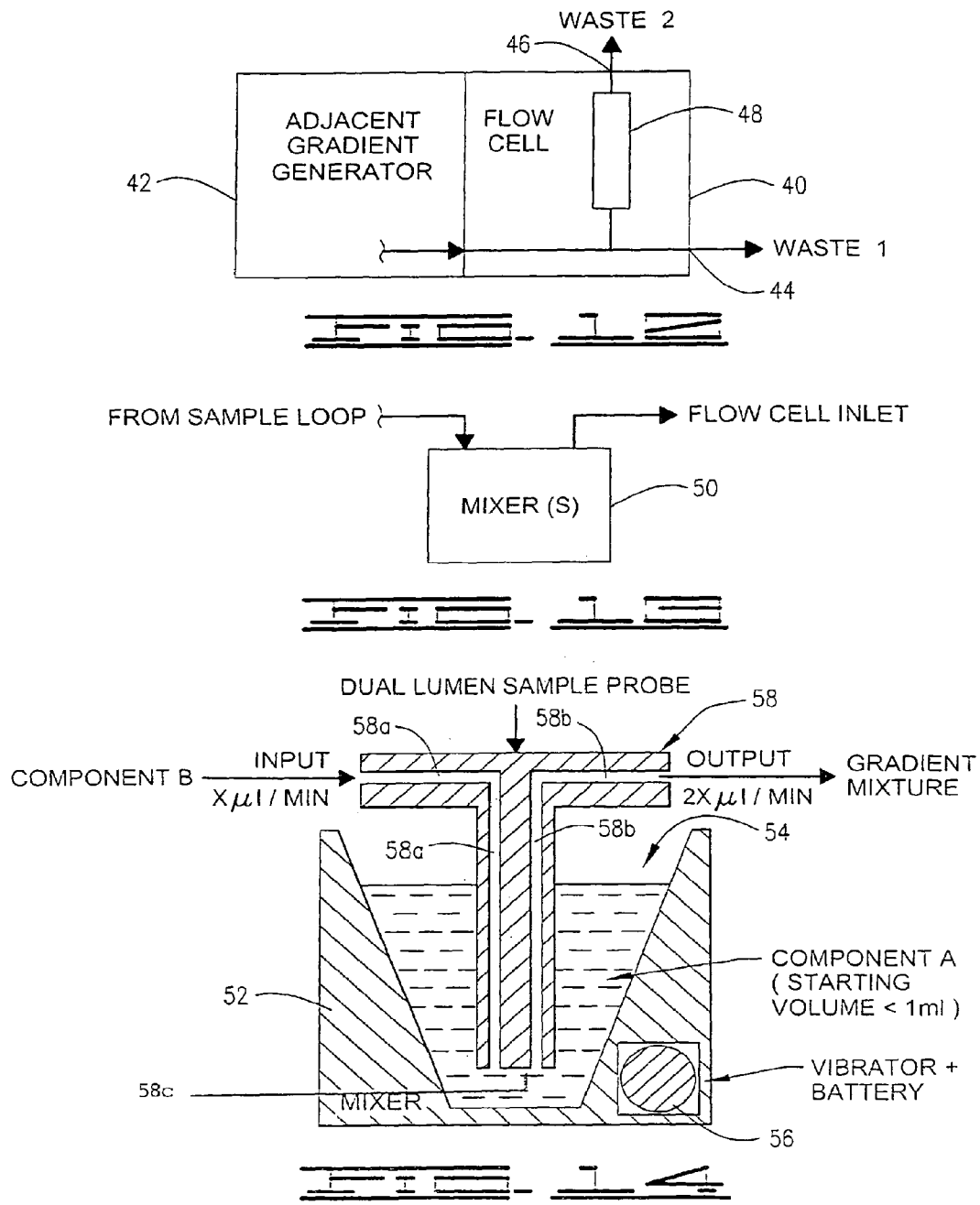

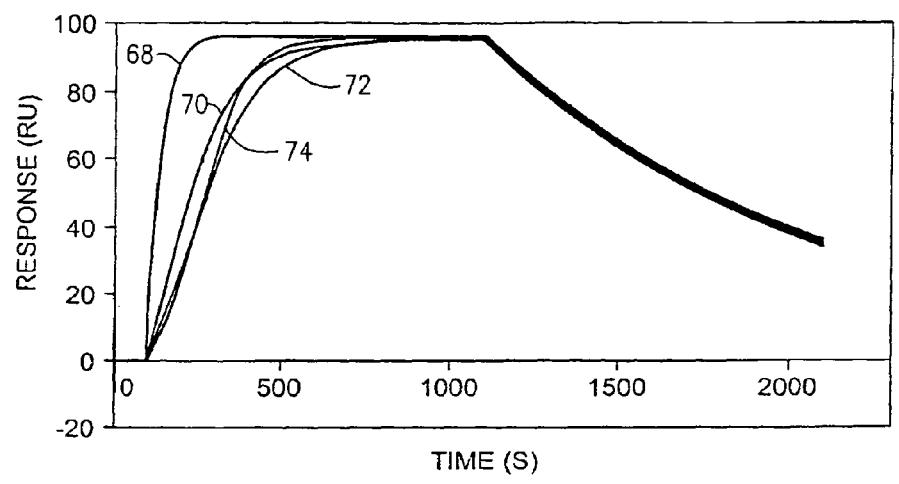
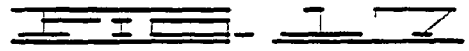
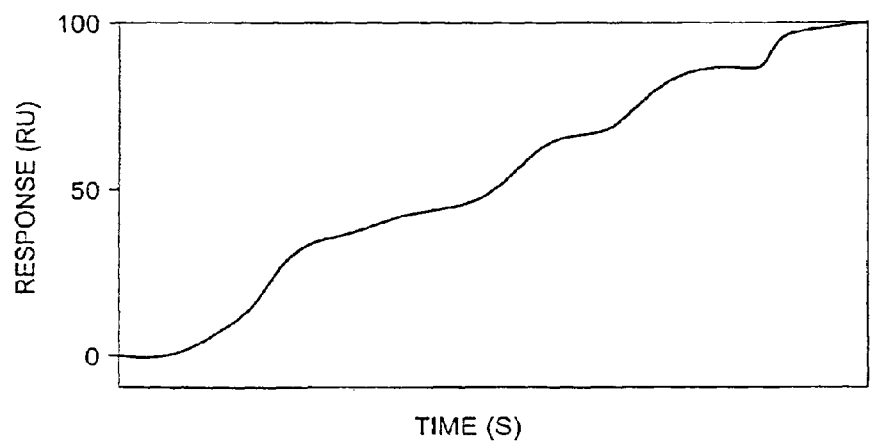
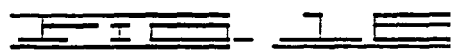

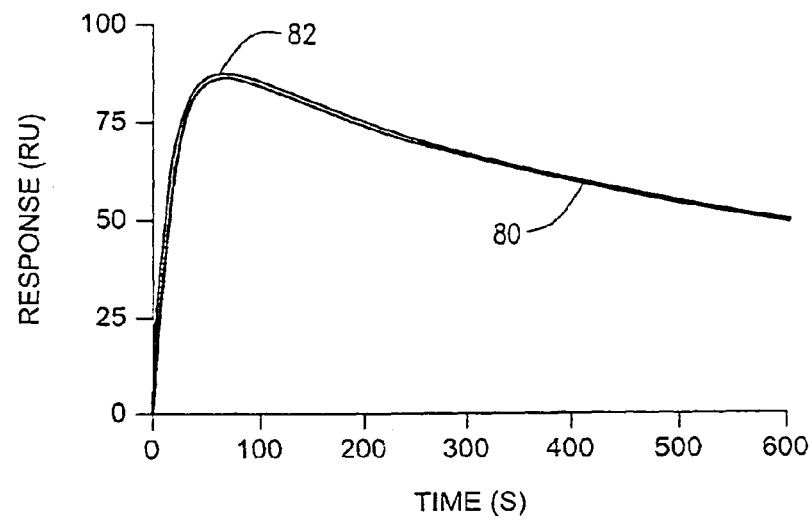
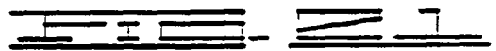
FIG. 21
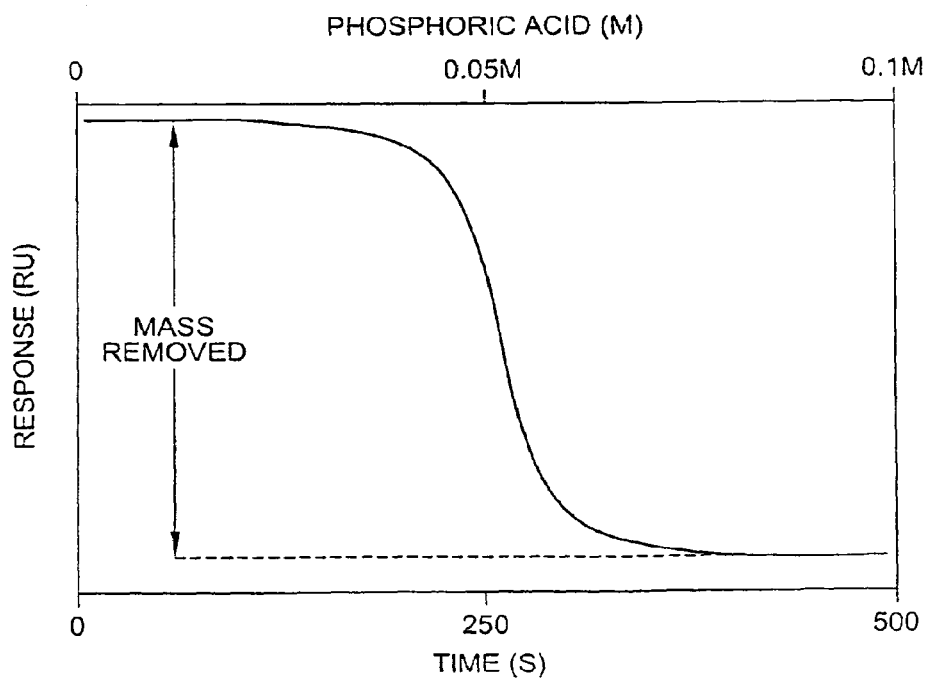
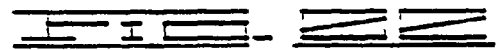
FIG. 22

US 8,906,672 B2

GRADIENT INJECTION FOR BIOSENSING

CROSS RELATED

This application claims the benefit of previously field International Application PCT/US08/00547 field Jan. 16, 2008, and United States Provisional Application Serial No. 60/965,640 field Aug. 20, 2007.

FIELD OF THE INVENTION

The present invention relates to fluidic systems and methods with which to inject flows of fluids relative to sensing regions. More specifically, the invention relates to providing and using single-injection concentration gradients wherein the gradient forming means is integrated into the biosensing system. One particular field of application is microfluidic biosensing using biomolecular ligands and analytes.

BACKGROUND OF THE INVENTION

Analytical instruments such as biosensors are well established as a means of recording the progress of biomolecular interactions in real time. Biosensors employ a variety of transduction technologies to detect interactions between biomolecules. Such instrumentation requires microfluidic channels in order to deliver samples to a sensing region, and pumps and valves are preferred means for moving sample through the channels in a controlled reproducible manner.

Recent interest in microfluidics technology has come about because of a growing need for sophisticated control of fluid streams for such sensing applications. A number of prior systems, referred to as integrated microfluidic cards, are composed of a series of substantially planar substrates possessing channels and structures that when bonded form internal passages and active components such as valves and pumps. Despite much progress these systems are rarely as robust as conventional flow injection analysis fluidic systems where the active components are not integrated into the fluidic card; however, these non-integrated systems typically have relatively large dead volumes.

There are several transducers capable of recording the progress of the biomolecular interactions to be detected. One example is a quartz crystal microbalance. Binding of molecules to the surface of a quartz crystal changes the fundamental resonance frequency which allows quantification of the binding event. Other technologies include light scattering, reflectometric interference spectroscopy, ellipsometry, fluorescence spectroscopy, calorimetry, and evanescent field based optical detection. A particularly effective evanescent field based technology, known as surface plasmon resonance (SPR), exploits the behavior of light upon reflection from a gold-coated optical substrate, for example.

SPR is an optical technique that enables real-time monitoring of changes in the refractive index of a thin film close to the sensing surface where materials to be tested are located (typical material types include a ligand attached to the sensing surface, a fluid buffer, and a fluid analyte which is contained (e.g. soluble or insoluble colloidal solution) in a running/flowing material that is to bind with the ligand and be tested). The evanescent field created at the surface decays exponentially from the surface and falls to one third of its maximum intensity at approximately 300 nanometers (nm) from the surface. Hence the SPR technique is sensitive to surface refractive index changes.

The delivery of samples to the SPR active sensing regions is made possible by creating flow channels that cover the active sensing regions. Each flow channel possesses an inlet and outlet to allow for the flow of buffer or samples over the SPR active sensing regions. The thin film sensing surface is derivatized to possess a polymeric coating that enables biomolecules ("ligands") to be permanently immobilized on the coating. The immobilized biomolecules usually possess binding specificity for another biomolecule contained in the sample (the "analyte"). The strength of this binding is given by the affinity constant which is simply the ratio of the binding rate constant divided by the dissociation rate constant. It is possible to measure these constants because an SPR-based biosensor records the progress of binding and dissociation events in real time.

Of particular interest is the kinetic analysis of such interactions. Important constants to measure include the association and dissociation between analyte in the flowing sample and ligands immobilized onto the sensing area. Other factors (e.g., mass transport characteristics of the sample) are also important to know. These are determined by flowing liquid mixtures containing one or more compounds (the analyte(s)) over sensing areas on which receptor chemicals (the ligand(s)) are located to interact with reactive contents of the mixtures. Using different concentrations of samples (i.e., different amounts of the one or more analytes in the mixtures) is important to enable such characteristics to be measured accurately.

There are different ways of achieving multiple concentration information from these known types of systems. One conventional way is to use different injectable volumes of solutions, each having a different concentration. One solution is flowed across the sensing area and data collected. The sensing area is then regenerated by flowing a "cleansing" fluid over the sensing area to remove the previous sample's contents. That is, usually when an analyte binds to an immobilized ligand the interaction must be reversed ("regenerated") in order to run another analyte injection. However, regenerating the surface can damage some of the immobilized ligand thereby resulting in decreased surface capacity for a subsequent test.

Sequentially injected volumes of solutions with different concentrations can be used without regeneration as disclosed in WO 2004/109284. In this step injection approach, the analyte is injected in a first volume at a low concentration then followed by a higher concentration in another volume and so forth until the surface is saturated. In this way it is possible to obtain data representing binding at different concentrations without using regeneration. These different concentrations also can be obtained from a mixture having a varying concentration within itself. See, also, WO 2004/109295, US 2003/0143565, and "Nonregeneration protocol for surface plasmon resonance: Study of high affinity interaction with high density biosensors." Tang, Y., Mernaugh, R. and Zeng, X. (2006), Anal. Chem., 78, 1841-1848.

According to "Analyte gradient-surface plasmon resonance: A one-step method for determining kinetic rates and macromolecular binding affinities." Shank-Retzlaff, M. L. and Sligar, S. G. (2000), Anal. Chem., 72, 4212-4220, regeneration of a surface can be avoided by continuously injecting a sample in which a concentration gradient exists due to operation of an in-line gradient maker. The kinetic models used for processing the data to determine the desired kinetic constants are modified to account for the changing analyte concentration during the single injection.

SUMMARY OF INVENTION

The present invention includes a method of providing, immediately adjacent to or within a flow cell, a gradient of concentrations that facilitates kinetic analysis of interactions without requiring multiple discrete volumes or injections to achieve a range of concentrations. This gradient is preferably formed directly adjacent to the flow cell inlet or in what is typically a region of sample/buffer dispersion at an injection point into a flow channel of a flow cell. Also included in novel aspects of the present invention are a gradient generating apparatus and method to obtain desired gradients; however, various embodiments of the present invention can be implemented using existing fluidics systems. The gradient may be of a type that is reproducible, or it may be one that is not. In either event, however, the present invention enables the gradient to be determined and used in kinetic analysis.

As mentioned, a continuous gradient fluid, having a varying concentration of a component in a carrier fluid, is created either within and along at least a portion of a sample holding channel connected to a flow cell or inside the flow cell itself. The continuous gradient fluid is injected, in a continuous injection, directly into the flow cell or the sensing region in the flow cell. Without limiting broader aspects of the present invention, various components and gradients are included herein.

The analyte gradient method of the present invention can characterize binding interactions between the analyte of the concentration gradient and an analyte binding species that is immobilized onto one or more sensing regions within a flow cell having a first portion of a first liquid disposed therein. This method comprises mixing a liquid sample, containing one or more analytes, with a second portion of the first liquid contiguous with the first portion of the first liquid such that a continuous analyte concentration gradient is generated in the second portion of the first liquid. This analyte gradient is flowed through the flow cell from a low analyte concentration to a high analyte concentration.

Furthermore, this invention can provide multiple component gradients. For example, if these gradients are for two molecules (A and B) that possess affinity towards each other, the ratio of the two reactants at any point in the gradient will change. Once created, the two components are allowed to approach binding equilibrium and the concentration of uncomplexed component B is determined in a biosensor concentration assay. In a preferred embodiment, a mass transport limited concentration assay may be used to reveal the concentration of B along the gradient and this is then plotted as a function of the concentration of A, and an affinity model fitted. The advantage in this method is that a single injection can be used to reveal the affinity constant for the interaction (conventional affinity assays can require multiple concentrations and several hours to complete, which may not be possible where reagent stability is poor).

In another aspect of the present invention, a gradient injection method within a biosensor provides a gradient profile determined by adjusting the composition of at least one of the solutions comprising the gradient such that a bulk refractive index difference exists between the gradient component solutions. The gradient is then injected over one, or more, sensing surfaces. The method further includes recording the biosensor's response to the bulk refractive index change during the gradient injection in order to determine the relative fraction of each gradient component solution present at the sensing surface(s) at all times during the gradient injection.

One or more of the following can be achieved in various implementations of the present invention. Regeneration is not required. A single injection now achieves the binding of analyte to immobilized ligand over a wide concentration range thus lowering the error associated with determining the kinetic constants using non-linear curve fitting. There is no need to prepare multiple samples. Dependence on prior knowledge of the saturating concentration is less critical as the gradient profile ensures that the concentration is varied over a very large range. This method may be employed to produce a single injection dose response curve.

Therefore from the foregoing, it is a general object of the present invention to provide novel and improved method and apparatus for providing or using a single injection gradient within a biosensor. Other and further objects, features, definitions, and advantages of the present invention will be readily apparent to those skilled in the art when the following description of the preferred embodiments is read in conjunction with the accompanying drawings.

BRIEF DESCRIPTION OF THE DRAWINGS

FIG. 1 is a block representation of a prior art biosensor with which the present invention may be implemented.

FIG. 2A is a schematic drawing of a prior art sample loop and sample loop valve used to input buffer and sample flows into the flow cell of FIG. 1, for example.

FIG. 5 shows a curve (in refractive units) responsive to changing bulk refractive index for an injected sucrose gradient.

FIG. 6 is a normalized graph of the response shown in FIG. 5.

FIG. 7 shows a sigmoidal model curve fitted substantially coincident with the normalized curve of FIG. 6.

FIG. 11 is a graph representing another exponential concentration gradient.

FIG. 12 is a block diagram representing a flow cell and adjacent gradient generator which may be used to achieve, for example, a linear gradient from a sigmoidal gradient in one implementation of the present invention.

FIG. 13 is a block diagram relating to an implementation with which to obtain an exponential gradient.

FIG. 14 is a schematic diagram of a micro mixer with which to obtain various gradients for the present invention.

FIG. 17 is a graph of response curves for four simulations: single concentration sample, linear gradient, exponential gradient, and sigmoidal gradient.

FIG. 18 illustrates a more complex gradient profile.

FIG. 19 is the gradient of FIG. 18 normalized by using an expected maximum bulk refractive index response.

FIG. 20 is a simulated response (and coincident fitted model curve) from which an affinity constant was determined from a single injection.

FIG. 21 is a simulated response (and coincident fitted model curve) from which correct kinetic values of an interaction of inhibitor with ligand were obtained from a single injection.

FIG. 22 is a graph showing an ideal response curve for a gradient of phosphoric acid such as used to determine a concentration at which dissociation of analyte-ligand complexes begins.

DETAILED DISCLOSURE OF THE INVENTION

Figure 2B:
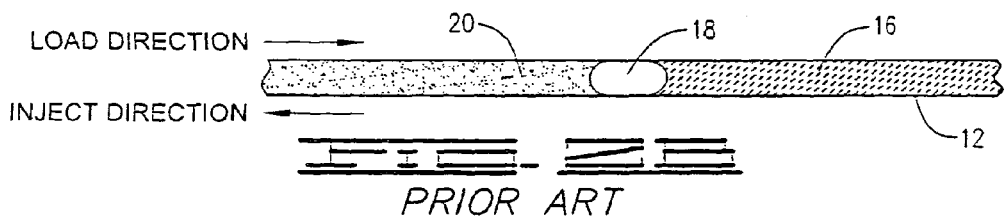
FIG. 2B represents a prior art buffer/sample interface such as could be used in the sample loop illustrated in FIG. 2A.

A conventional biosensor 2 of any type with which the present invention can be used is represented in FIG. 1. Such a biosensor 2 includes one or more flow cells 4 in which there are one or more sensing areas having one or more types of molecules (referred to as ligands or analyte binding species) which are immobilized thereon and with which one or more types of molecules (referred to an analytes) can form binding reactions (e.g., associate with and dissociate from) in known manner.

Sample containing analyte is input to such a flow cell through suitable fluid flow components 6 that connect directly to the flow cell inlet. The fluid flow components 6 provide an elongated sample holding channel connected directly to the inlet of the flow cell. This sample holding channel is adjacent to the flow cell, and it is where the gradient is created in accordance with one aspect of the present invention so that the gradient can be directly communicated into the flow cell. The sample holding channel preferably has a volume not less than (or equivalently, greater than or equal to) the volume of sample to be used. In another aspect of the invention, the gradient can be created within the flow cell itself.

One or more fluid sources 8 provide sample, or components for the sample, to the fluid flow components 6 (sample in general typically includes one or more analytes and one or more liquids to carry the analyte(s), such carrier fluid(s) including sample buffers or other analyte-containing liquids if multiple analyte samples are used). Conventional types of sources include syringes and other manual injectors as well as automated sources, such as autosamplers, for example. The fluid sources 8 also provide one or more types of buffer (a non-reactive liquid with no analyte) of known functions and compositions.

The fluids, typically liquids with regard to biosensors, are loaded into the sample holding channel of the components 6 (or within the flow cell itself) such that one fluid partially displaces another fluid previously in the channel or flow cell and thereby causes the gradient to form. Buffer can be loaded first followed by sample or vice versa depending on a particular gradient that is desired or sequencing within the overall system. However, in general, sample will be flowed across a sensing area from low concentration end to high concentration end of the gradient sample.

When sample is input to the flow cell 4, association and dissociation reactions between the analyte and ligand materials change the refractive index in an SPR type of biosensor, for example; of whatever type biosensor, these reactions are sensed, data is collected, and analyses made in suitable components defining the one or more systems 10 indicated in FIG. 1.

As a particular example, one type of SPR biosensor includes a laser, a polarizer, a prism, a gold slide, and a photodiode detector as known in the art. The photodiode detector responds to the refractive index of the gold slide as affected by association and dissociation reactions between analyte in the sample flow and ligands on the gold slide. Data signals from the detector can be stored, but the data are ultimately used in numerical processing components of the systems 10 as known in the art (for example, microprocessor-based circuits programmed with suitable algorithmic and control software).

In general, preferred embodiments of the present invention can be implemented using any suitable type of biosensor with which different concentrations of one or more analytes can be provided in a single injection and the association, dissociation, and also preferably mass transport, data collected. Some analytical aspects are also included in the present invention, but as an adjunct to numerical processing techniques already used in such biosensors.

Referring to FIG. 2A, one implementation of fluid flow components 6 which can be adapted for the present invention includes a conventional sample loop 12 connected between two ports of a conventional flow injection analysis injector valve, such as a six-port two-position sample loop valve 14. In conventional use, buffer is supplied by a pump (not shown but constituting one type of fluid source 8) and flows from the pump into a buffer input port of the valve 14 and directly out another port of the valve 14 through a connecting conduit 15 into the flow cell 4 when the rotary valve is in its "load" position. When in the load position, sample (that is, the fluid containing analyte) may be loaded manually using a syringe or automatically using an autosampler, for example (such syringe, autosampler, or other sample loading component is part of the fluid sources 8 of FIG. 1). An autosampler is preferable for optimum reproducibility. Loading occurs through the "load loop" or "inject port," as labeled in FIG. 2A, into the sample loop 12. Flow out of the sample loop 12 in this valve setting exits through the "loop waste" port of the valve 14.

A flow injection system as shown in FIGS. 1 and 2A can be used to perform conventional injections known in the art and gradient injections of the present invention. When performing a conventional injection, air bubbles may be used to prevent the sample from mixing with buffer already contained in the sample loop. In conventional flow injection, the ports of the valve 14 and connections to the ports are arranged such that sample loaded into the loop in one direction flows in the opposite direction when the valve 14 is switched to "inject," whereby the contents of the sample loop 12 flow into the flow cell. This allows sample contained in a partially filled loop to enter the flow cell without a delay. This is represented in FIG. 2B in which buffer 16 previously in the sample loop 12 (such as during a previous "inject" state of the valve 14, which connects the buffer inlet port of the valve 14 to the sample loop as apparent from FIG. 2A) is separated by air bubble 18 from sample 20 loaded with the valve 14 in its load state. The load direction is to the right in FIG. 2B, and the inject direction is to the left in FIG. 2B.

Figure 3A:
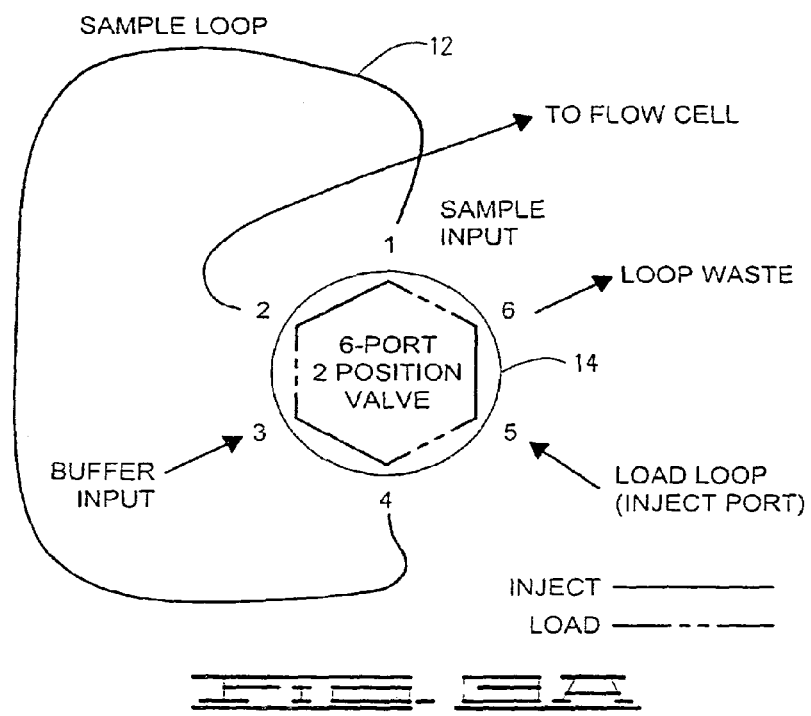
FIG. 3A is a schematic drawing of the components of FIG. 2A adapted to implement one embodiment of the present invention.

FIG. 3 shows a gradient created using one approach of the present invention. In this approach the sample input ("load loop") and sample output ("loop waste") ports of the valve 14 are reversed in order to ensure that the gradient flows into the flow cell from low to high concentration. This is shown in FIG. 3A, where the "load loop" and "loop waste" functions are reversed from the conventional orientation shown in FIG. 2A. So, the same sample loop 12 and sample loop valve 14 are used, just the flows to and from these two ports of the valve 14 are changed. The six-port two-position valve 14 still rotates between an inject state and a sample load state, but by rearranging the sample load port and loop waste port as shown in FIG. 3A the sample that enters the loop first also exits first ("first-in, first-out").

Figure 3B:
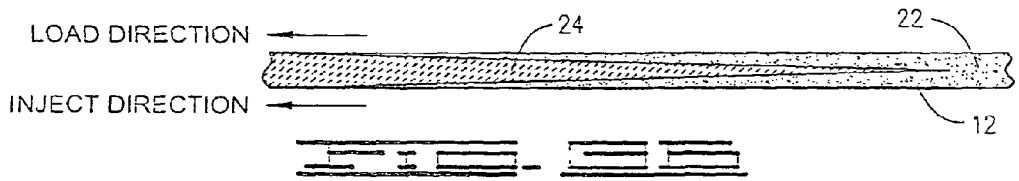
FIG. 3B represents a single-injection concentration gradient provided by the present invention using the configuration shown in FIG. 3A.

Continuing with this example of the present invention, there is buffer in the sample loop 12 as before in the conventional load and injection of FIG. 2 (if not, it can be put in the sample loop by switching the valve 14 to its inject state and then flowing buffer into the sample loop 12). This portion of buffer in the sample loop 12 is contiguous to a portion of buffer in the conduit 15 and the flow cell 4. In the present invention, however, when the valve 14 is put in its load state, sample is flowed into the lower end of the sample loop 12 ("lower" as viewed in FIG. 3A). For example, an air bubble is first aspirated into a syringe of fluid source 8 followed by sample; a terminal bubble, at what becomes the head or leading end of the sample upon loading and injecting, is not required. The sample is then loaded from the syringe into the sample loop through the new load loop port of the valve 14. Since there is no terminal bubble separating the leading end of sample from the buffer already present in the sample loop, mixing will occur along the longitudinal volume in the sample loop where these fluids come together. This loads the sample in a first-in, first-out manner opposite to the aforementioned conventional, prior art technique. That is, in the present invention the first part of the sample loaded into the sample loop is also the first part of the sample injected into the flow cell. This is illustrated in FIG. 3B in which a concentration gradient has been formed as the leading portion of sample 22 has been forced into mixing with the tail portion of buffer 24. The profile of a gradient created in this manner will always be sigmoidal when optimized. However, changing the rate at which the second component is injected will change the slope of the curve. In addition the relative volumes of each sample may be altered to change the overall gradient profile. Sigmoidal curves are common in biological science and are usually modeled using a 4-parameter logistic equation. In FIG. 3B there is relatively little sample at the leading edge (the first-in portion of the sample), but the concentration increases toward the main body (last-in portion) of the sample. Thus, this is one way in which the present invention actively shapes the concentration gradient between at least two fluids inside the sample loop. It is to be noted that FIG. 3B is drawn to illustrate relative amounts of buffer and sample along the length of the interface; however, in practice these amounts will be intermixed across the cross-sectional areas. That is, in practice the ratios of sample to buffer are present within differential length segments of the interfaced or dispersed region, but the liquids are mixed and there is not a distinct buffer/sample separation line in these segments.

Figure 3C:
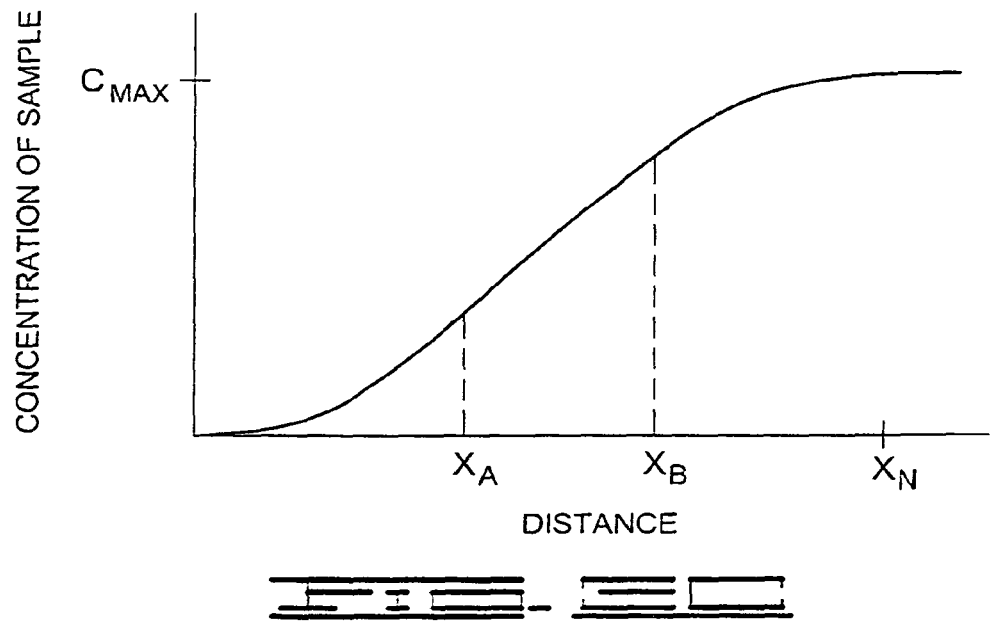
FIG. 3C is a graph representing the concentration gradient of the sample shown in FIG. 3B.

The change in concentration along the length of the dispersed sample/buffer interface is represented by the graph of FIG. 3C (the 0 distance point of the graph corresponds to the left end of the sample loop section as oriented in FIG. 3B; the $X_N$ point corresponds to the point in the sample loop 12 where 100% sample begins). This graph shows a sigmoidal gradient. The sigmoidal concentration gradient is well characterized by a known sigmoidal 4-parameter logistic expression. The presence of the air bubble aspirated into the loading syringe, which air bubble becomes at the tailing end of the sample within the loop in the FIG. 3 example, prevents mixing of the injection-driving buffer at the tailing end of the sample. If such mixing occurred, it would result in a more complex gradient profile.

Preferably a concentration gradient is selected that will ensure saturation of the sensing surface of the flow cell in reasonable time. Once the desired gradient has been established in the FIG. 3 example, the valve 14 is switched to its inject state and the contents of the sample loop 12 are then injected into the flow cell 4 in conventional manner. For example, another portion of buffer is flowed through the buffer input port of the valve 14 of FIG. 3A and against a last-in end of the sample so that this additional portion of buffer pushes the gradient of sample out of the sample loop 12 and through the conduit 15 into the flow cell. Preferably injecting occurs in a single continuous injection with the gradient sample fluid flowing directly from the sample loop into the flow cell through as short a conduit 15 as possible. So as not to mask binding reactions for different concentrations, the gradient should be injected into the flow cell so that the lowest concentration end of the sample enters first and the highest concentration end enters last. This occurs with the gradient shown in FIG. 3B, for example.

Figure 4:
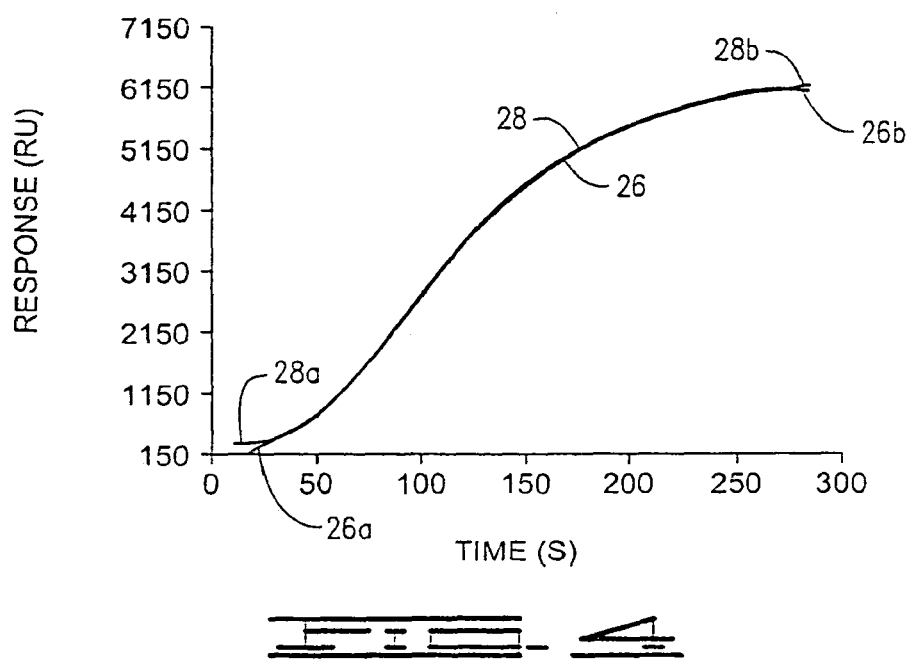
FIG. 4 is a graph representing the change in refractive index for an SPR type biosensor for a simulation corresponding to a continuous injection of the concentration gradient of FIG. 3C.

To determine the sigmoidal profile described above with reference to FIG. 3, a sample gradient was produced as described. Specifically, a high index solution (i.e. sucrose in water) was employed to form the gradient. FIG. 4 shows the detected response and fitted curves. In FIG. 4 curve 26 is the refractive index response curve obtained from injecting a loop loaded with a sucrose-in-water sigmoidal gradient obtained as described above with reference to FIG. 3. Curve 28 is the fitted expression. The fitted curve 28 is a good approximation of the actual curve (deviations visible in FIG. 4 occurring only at curve ends 28a, 28b relative to actual data curve ends 26a, 26b) and hence the expression for the curve may be used to describe the changing concentration of injected analyte during a sigmoidal gradient kinetic injection. So, the changing concentration can be mathematically defined and inserted into known processing algorithms for determining kinetic characteristics of the analyte/ligand reactions.

An example of one type of algorithm for determining kinetic constants is the conventional two-compartment interaction model given by the following set of differential equations. These equations are solved by numerical integration, or by finding an exact analytical solution, and then applying non-linear curve fitting to find the optimum parameter values.

$A = \text{Conc}$ $A_0 = 0$ $dA/dt = kt^*(\text{Conc}-A) - (ka^*A^*B - kd^*AB)$ $B_0 = R\max$ $dB/dt = -(ka^*A^*B - kd^*AB)$ $AB_0 = 0$ $dAB/dt = (ka^*A^*B - kd^*AB)$ Total response:

$AB + RI$ where A=analyte concentration at surface
B ligand concentration
ka=association rate constant
kd=dissociation rate constant
Conc=injected analyte concentration AB=complexes formed from A+B
kt=mass transport constant
Rmax=maximum analyte binding response
RI=bulk refractive index response Notice that the concentration of analyte (A) at the surface is governed by the mass transport constant, kt. If kt is large, then A is a good approximation of Conc. When doing a gradient injection, A will also be changing with respect to time. Hence this change may be included by simply multiplying A by some function G that describes the gradient profile and hence the analyte concentration at all times (t).

Thus $$A = G * Conc$$

In FIGS. 3B, 3C the gradient is sigmoidal and that is described by the following 4-parameter logistic function.

$$G = Rhi - ((Rhi - Rlo)/(1 + (t/A)^B))$$

where

Rhi, Rlo, A &B are all fitted parameters.

In more detail, the concentration of analyte along a gradient prepared according to the present invention is to be determined if the gradient injection response is to be used for kinetic analysis. Only the maximum analyte concentration is known and the analyte concentration along the gradient remains unknown unless a well defined gradient forming means is employed where the gradient function (i.e. exact function defining the analyte concentration at all times during the injection) is also known. Fitting the analyte concentration along the gradient as an unknown parameter during kinetic/affinity model fitting may yield reasonable results, but it is preferable if the analyte concentration along the gradient can be unambiguously determined. To this end it is possible to reveal the analyte gradient by adding a component to the sample that will give rise to a bulk refractive index offset between both components of the gradient. Then when mixed in various proportions as the gradient is made, the relative fraction of each component may be determined from the bulk refractive index response. In effect both an analyte gradient and a sucrose gradient (for example) that are complementary are prepared in the same gradient sample. Alternatively if it can be assumed that gradient formation and injection are highly reproducible, then the sucrose gradient injection may be prepared and injected separate from the analyte injection. Once the gradient is defined in this way for a particular set of gradient formation and injection conditions then that definition may be stored and used in future experiments. If significant variability is expected in analyte gradient formation and injection, then a bulk index gradient should be added to the analyte gradient. Sucrose is a convenient additive as standards of known refractive index are easily prepared from brix value tables used in the beverage/soft drinks industry. However, a large variety of other substances may be employed; examples include hydrophilic polymers, carbohydrates, glycols and water miscible solvents.

Accordingly, the present invention includes a gradient injection method for use with a biosensor (such as an optical biosensor, for example). In this method a gradient profile is determined by adjusting the composition of at least one of the solutions comprising the gradient such that a bulk refractive index difference exists between the gradient component solutions. This gradient is injected over one, or more, sensing surfaces. The biosensor's response to the bulk refractive index change during the gradient injection is recorded in order to determine the relative fraction of each gradient component solution present at the sensing surface(s) at all times during the gradient injection.

In one implementation, the gradient in bulk refractive index possesses a complementary gradient in analyte concentration wherein the gradient is injected over two, or more, sensing surfaces wherein the analyte gradient composition is inferred from the bulk refractive index response recorded over a sensing surface that does not possess affinity binding ligands for the analyte. More specifically, the gradient in bulk refractive index can possess a complementary gradient in one, or more, analytes, which overall composition is injected over first and second sensing surfaces. The first sensing surface is coated with a capture material that possesses affinity for one, or more, of the analytes contained in the gradient, and the response from the first sensing surface represents contributions from both the bulk refractive index changes and the surface refractive index changes that result from analyte binding to the capture material. The second sensing surface is not coated with the affinity capture material and the biosensor response from the second sensing surface represents bulk refractive index changes without analyte binding and is used to infer the analyte gradient composition during the injection. The response due to one, or more, analytes binding to the first surface is resolved by subtracting, or dividing, the response of the second sensing surface from the response from the first sensing surface. For example, the bulk refractive response from the second channel is used to infer the concentration of the complementary analyte(s) gradient by dividing the response by the maximum expected response for a 100% pure solution of the higher refractive index gradient component, then fitting an equation using a regression curve fitting procedure that suitably models the profile of the gradient as a function of injection time, and then multiplying the starting analyte concentration used in preparing the gradient by this gradient function in order to estimate the analyte concentration as a function of time during the gradient injection. Even more particularly, the analyte gradient is complementary but opposite to the gradient in the high refractive index material, wherein if the gradient function is G then the starting analyte concentration is multiplied by 1-G to estimate the analyte concentration as a function of time during the gradient injection.

In another implementation, the gradient is injected over a single sensing surface and the individual contributions of analyte binding to immobilized ligand and bulk refractive index variation are resolved from a single response curve as a function of injection time by employing non-linear regression curve fitting of predefined mathematical models.

The bulk refractive index of a gradient component solution may be adjusted by addition of any material or reagent that changes the refractive index of that solution but does not significantly interfere with analyte binding to immobilized ligand. Non-limiting examples include: sugars, polysaccharides, glycols, hydrogels, salts, hydrophilic polymers and water miscible solvents.

Next will be described the application of the invention as applied to kinetic analysis of the interaction of IL-2 with anti-IL2 antibody immobilized on the sensing surface. A sucrose gradient is prepared and injected, which gradient is of known refractive index using the same gradient preparation and injection parameters as are to be used for the actual analyte gradient injection. The optical biosensor responds to the changing bulk refractive index along the gradient giving a typical sigmoidal response curve 30 as shown in FIG. 5. The curve is y-normalized to yield a curve 32 with limits from 0 to 1.0 as shown in FIG. 6. The sigmoidal model [i.e. $G = Rhi - ((Rhi - Rlo)/(1 + (t/A)^B))$] is fitted to this curve 32 as shown by curve 34 in FIG. 7. All parameters are obtained from the model fit giving Rhi=1.016, Rlo=−0.2271, A=77.75 and B=0.009097. Thus the function G now defines the exact gradient profile for the gradient injection and is used to define the concentration of analyte in an analyte gradient prepared and injected in the same way. The two-compartment model as defined earlier is then fitted. Alternatively a simple model may be fitted as mass transport limitation is not as significant when a non-steady state concentration of analyte is present at the sensing surface. Therefore the simple model can be written as follows.

$A(\text{solution}) = \text{Conc}*gG$ $G = 1.016 - ((1.016 + 0.2271)/(1+(t/77.75)^{0.0091}))$ $A[0] = 0$ $B[0] = R\text{max}$ $dB/dt = -(ka*A*B - kd*AB)$ $AB[0] = 0$ $dAB/dt = (ka*A*B - kd*AB)$ Total response:

$AB + RI$

Figure 8:
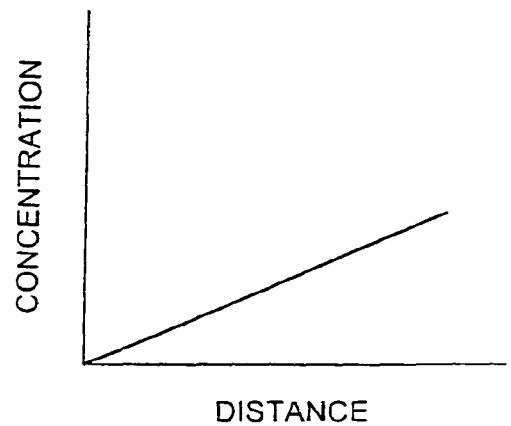
FIG. 8 shows both (1) an experimentally obtained binding response curve for a sigmoidal gradient injection of interleukin 2 over an anti-interleukin 2 antibody coated surface and (2) the fitted model curve.

The experimental binding response curve shown in FIG. 8 is for the injection of a sigmoidal gradient of interleukin 2 (IL-2) over a surface coated with anti-IL-2 antibody (i.e. ligand). The gradient volume was 125 μL and was injected at 25 μL/min. The bound IL-2 was then allowed to dissociate (i.e. exponentially decaying phase) for about 400 seconds. The graph includes actual IL-2 binding curve 36 and the fitted model curve 38. The kinetic constants were $ka = 3.2 \times 10^5$ M$^{-1}$ s$^{-1}$, $kd = 1.6 \times 10^{-3}$ s$^{-1}$ and KD=5 nM (KD is the dissociation affinity constant=kd/ka). These values are in agreement with interaction constants determined by conventional kinetic analysis employing multiple fixed concentration injections.

In another embodiment the injection flow rate may be changed "on-the-fly" as the gradient is being injected. This causes a step profile in the gradient even though the injected gradient itself is a continuous gradient.

Figure 9:
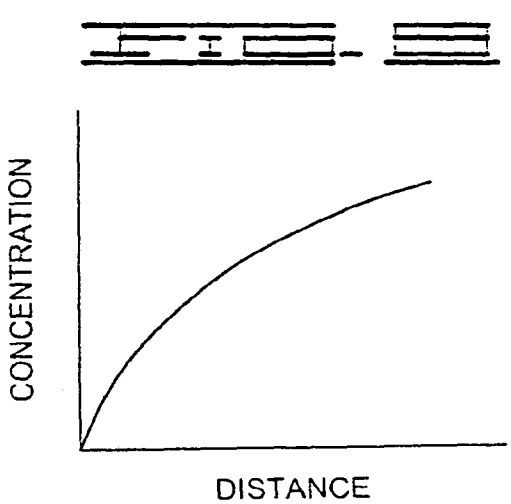
FIG. 9 is a graph representing a linear concentration gradient.
Figure 10:
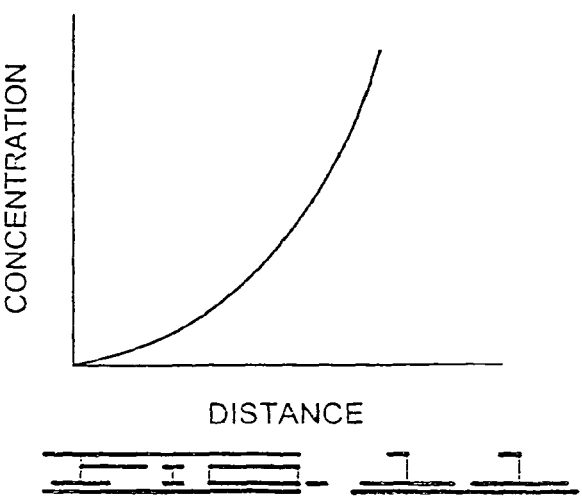
FIG. 10 is a graph representing an exponential concentration gradient.

In general, a wide variety of gradient profiles may be generated by modifying the sample injection method. Examples, which do not limit other gradients that are within the scope of this invention, are shown in FIGS. 9-11. FIG. 9 illustrates a linearly increasing concentration of sample. FIGS. 10 and 11 illustrate two different exponentially increasing gradients of sample.

FIG. 12 illustrates components that can be used to provide one method of obtaining a linear gradient. This is one example of another aspect of the present invention whereby a selected portion of continuous gradient fluid can be used. This is not a step or segmented injection because such selective injection is still performed in a single continuous injection such that an entire test event for a gradient of concentrations is obtained during the single continuous injection.

In the FIG. 12 illustration, the previously described sigmoidal gradient is formed in the sample loop as described with reference to FIG. 3. Notice that in FIG. 3C there is a substantially linear region, such as between points $X_A$ and $X_B$. To inject this gradient into flow cell 40 from adjacent gradient generator 42 in accordance with this implementation of the present invention, the injection first proceeds with waste 1 port 44 open and waste 2 port 46 closed so that the portion of gradient sample from point 0 to point $X_A$ is removed (i.e., this non-linear portion flows to waste) and then port 44 is closed and port 46 opened so that the substantially linear $X_A$ to $X_B$ portion flows over the sensing region 48 of the flow cell 40. Port control then reverses the states of the ports 44, 46 to flow the remainder of the gradient to waste (the remaining, non-linear, portion after point $X_B$).

Referring to FIG. 13, an exponential gradient can be obtained by using a closed mixer 50 as further described below. Such a mixer 50 if used for the present invention is placed in effect where the conduit 15 of the sample loop embodiment is, that is, for direct input into the flow cell. Putting two of these in series can be used to obtain two different exponential gradients. Also, a linear gradient may be obtained if the volume inside the mixing chamber of the gradient maker is decreased incrementally during gradient formation by drawing more liquid from the mixer than is added. A highly linear gradient in analyte exists if the ratio of the input flow rate to the output flow rate is 0.588. In many cases a sufficiently linear gradient will be produced if the ratio is 0.5. Linear gradients formed in this way deviate substantially from linearity over the final 15% of the gradient so this segment is usually discarded.

For use in the two-compartment model referred to above, for example, a linear gradient assumes that the concentration of analyte varies linearly and may be described as follows:

$A = C*t$ where
  C is the incremental increase in concentration per second and
  t is time of flow (seconds).

An exponential concentration gradient can be created by injecting sample into a closed volume that is then mixed. At the beginning the concentration of sample in the closed volume is zero, but once the injection begins the sample displaces the liquid in the closed volume. The displaced liquid flows to the flow cell. Thus, steps of this implementation of the present invention include: flowing the liquid sample into the mixing chamber, operating the mixing chamber such that the liquid sample and other liquid in the mixing chamber are homogenously mixed and output to the flow cell as an increasing analyte gradient that is characterized as a smooth exponential analyte gradient. As the injection progresses the concentration of analyte in the displaced liquid flowing into the flow cell may be described as follows.

Mixing in other types of sample holding channels can be used. For example, the sample holding channel can include a barrel of a sample loading syringe or sample injection probe or injection needle. Another type, from which a variety of gradients can be obtained, is described next.

Means of Preparing a Gradient Integral with a Flow Injection Analysis (FIA) System.

In order to become a commercially viable approach to performing gradient injections it is vital that low volumes are used. Shank-Retzlaff and Sligar, cited above, prepared 18 milliliters (mL) of gradient solution using a standard gradient generator and then the output from the gradient generator was immediately pumped into a flow cell that was interrogated with an SPR detector. This 18 mL volume is in the region of 100-fold greater than would be generally acceptable for a commercially useful system. Therefore a means of preparing low volume gradients and integration with conventional low volume fluid handling systems is required. Also the system should be integrated with a high quality low volume flow injection analysis system.

Therefore, in another preferred embodiment of the current invention the gradient is prepared by employing a dual lumen sample probe to add, and remove, liquid from a miniature mixing container. The input/output flow rates are appropriately chosen to shape the gradient profile. Biosensors suitable for biomolecular interaction analysis are optimized for processing low sample volumes. Precision syringe pumps are employed for aspiration and dispensing low volumes of liquids.

The gradient making of this embodiment of the present invention is performed using a conventional auto-sampler fluidic configuration combined with an innovative micro mixing chamber. Conventional gradient makers accomplish mixing by employing a rotating magnetic stirrer situated in the bottom of the chamber. The large scale of these commercially available magnetic stirrers is not suitable for the generation of low volume gradients. It is possible to create gradients using commercially available gradient generators where the volumes required to produce a stable gradient exceed 50 mL. In biomolecular interaction analysis a volume of 0.5 mL is considered very large. This is due to the cost of reagents and the use of microfluidic sample deliver systems.

In one embodiment of this present invention as shown in FIG. 14, mixer 52 mixes the liquid in mixing chamber 54 by using a miniature vibrator 56 of any suitable type (e.g. miniature asymmetric motors, piezo crystals, acoustic/sonic). Mixing may also be accomplished by forming the inside of the mixer with structures such as baffles that cause turbulent mixing allowing well mixed liquid to flow into the output stream without requiring any other active mixing means. If mixing is not adequate, then the gradient suffers from distortions; however, these distortions may be exploited to generate many gradient profiles. The baffle arrangement may be suitably chosen to alter the gradient profile in a mixer characterized by imperfect mixing. The miniature mixer 52 may be located inside or close to the sample holding compartment of the auto-sampler system.

In FIG. 14 the gradient making apparatus also comprises a dual lumen probe 58 mounted on a robotic arm (such as a robotic arm of an auto-sampler system). Lumen 58a is connected to an input stream and lumen 58b is connected to an output stream. Each stream is connected to/created by a precision pump capable of dispersing or aspirating liquid. The robotic arm and pump(s) can be parts of a common auto-sampler configuration for dispensing and aspirating samples from discrete locations on a sample rack adjacent to the auto-sampler.

To generate a gradient in accordance with the present invention using the equipment depicted in FIG. 14 and described above, two sample vials filled with liquid component A and liquid component B, respectively, are loaded into the sample rack. The auto-sampler then aspirates a defined volume of component A and places it into the mixing chamber 54 of the mixer 52. The channels/lumens of the probe 58 are then rinsed out with wash liquid at a wash station of/adjacent the auto-sampler. Although either lumen can be an input or output, as shown in the particular example of FIG. 14 the auto-sampler is then operated to move the probe 58 to aspirate into lumen 58a a volume of component B that is equal to the volume of component A in the mixer. Tip 58c of the dual lumen probe 58 is then positioned at the bottom of the mixing chamber 54 that has the known volume of component A. To generate a linear gradient, component B is added into the mixing chamber 54, via lumen 58a, at a defined flow rate while mixed liquid (i.e. the gradient) is simultaneously removed via lumen 58b at a flow rate that is two-fold the input flow rate. The total volume of liquid inside the mixing chamber 54 decreases over time until there is no liquid remaining in the mixing chamber 54. A linear gradient in component B is recovered from the output of lumen 58b. The concentration of B at the beginning is zero and the concentration of B at the end is 100%.

The output stream may be immediately directed over one, or more, sensing regions for analysis whereby the gradient generation and analysis is performed simultaneously. It is also possible to store the gradient in a holding channel allowing the gradient to be injected at some later time. It is also possible to reverse the flow from the holding channel while directing the sample over the sensing region(s) thereby exposing the surface to the gradient in reverse. It is also possible to produce a reverse gradient profile by placing component B in the mixer and adding component A from the probe. A non-linear gradient may be generated by changing the mixer input/output flow rates. For example an exponentially decaying gradient may be produced by holding the volume inside the mixer constant by matching the input and output flow rates (i.e. input flow rate=output flow rate). Concave gradients may be produced by lowering the output flow rate relative to the inlet flow rate. In another embodiment it is also possible to produce multiphase gradients by changing the relative input/output flows on the fly. For example the gradient could possess a linear region followed by an exponential region.

Figure 15:
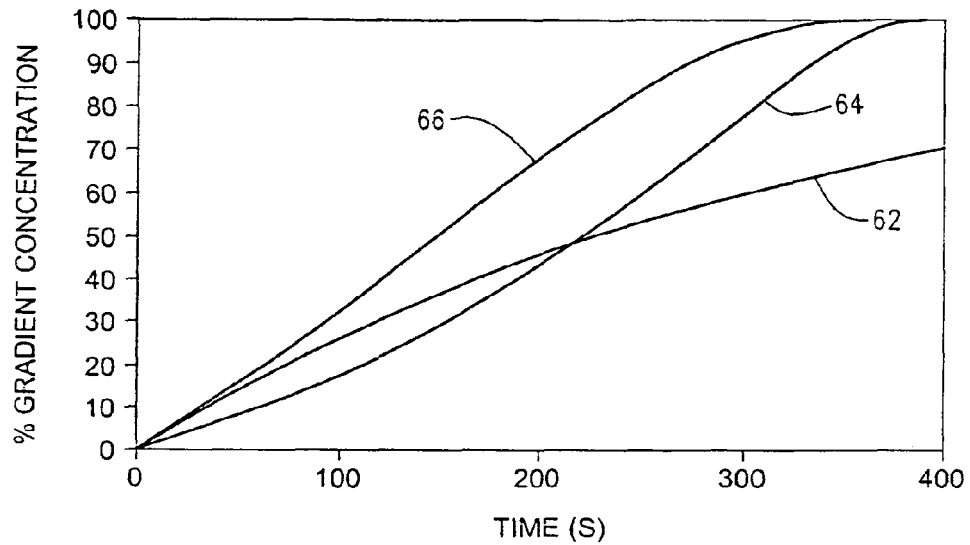
FIG. 15 shows three gradient profiles from a simulation using the present invention.

The profile of a gradient in component B produced by this gradient making device can be predicted by the following equation:

$$B(t) = B_{max} - (B_{max} * e^{(-F_{in}*t/V)})$$

where $B_{max}$=maximum concentration of component B
$F_{in}$=input flow rate
$V$=volume in mixer at time $t = V_0 + (F_{out} - F_{in})*t$, where
$V_0$=Volume in mixer at $t=0$ and $F_{out}$=Out flow rate FIG. 15 shows three gradient profiles simulated using the above equation. In FIG. 15: (1) convex gradient curve 62 resulted from equal input and output flow rates of 37 microliters per minute (μL/min) using a mixer volume of 200 μL; (2) concave gradient curve 64 resulted from an input flow rate of 37 μL/min, an output flow rate of 74 μL/min, and a mixer volume of 2004; and (3) linear gradient curve 66 resulted from an input flow rate of 37 μL/min, an output flow rate of 63 μL/min, and a mixer volume of 200 μL (note this curve 66 is approximately linear to 85%).

Figure 16:
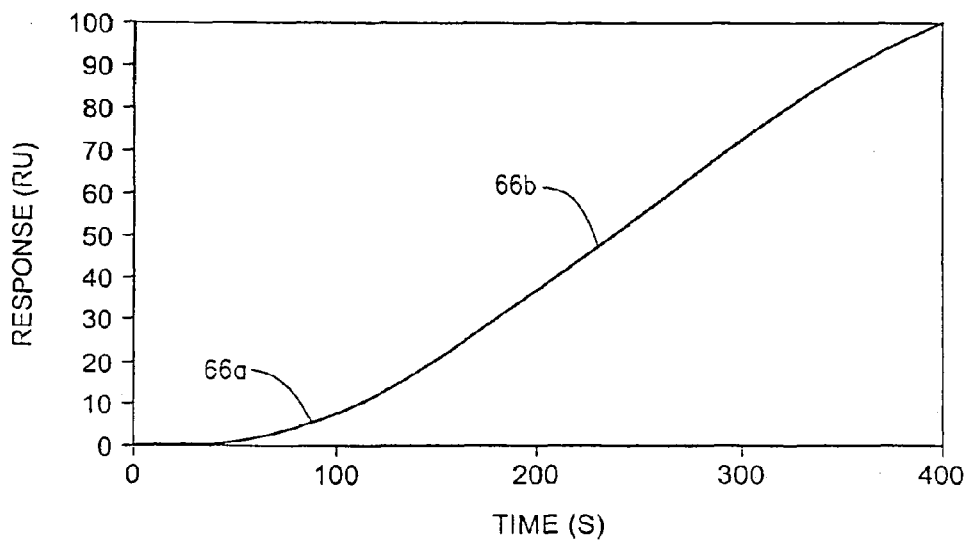
FIG. 16 is a graph showing a transformation of the substantially linear curve of FIG. 15 such that an exponential tail portion of the gradient of FIG. 15 is used and injected first.
Figure 15:
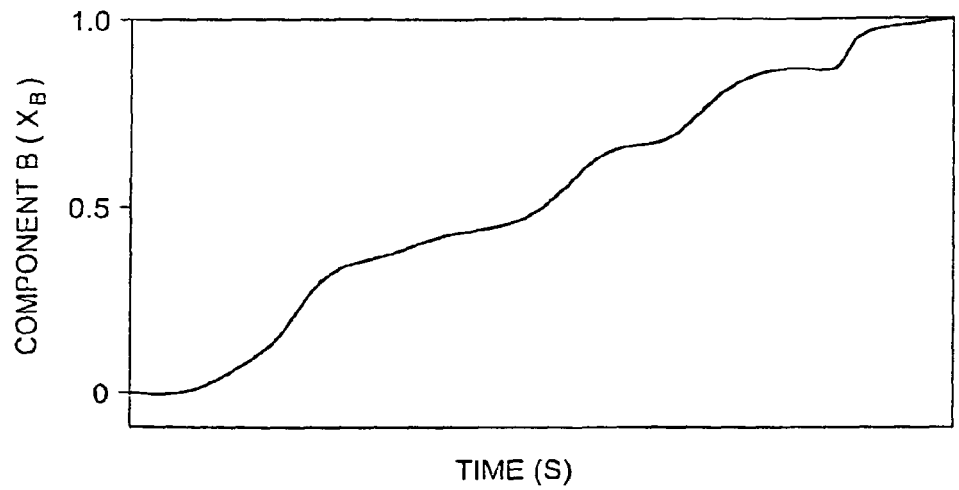
Figure 16:
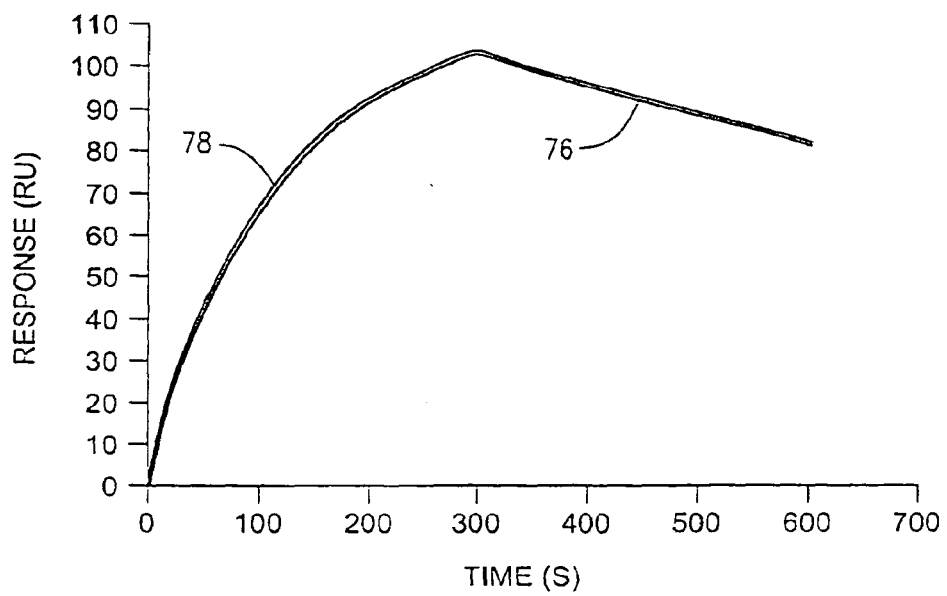

For the linear gradient shown in FIG. 15 the volume of liquid in the mixing chamber decreases because the output flow rate is higher than the input flow rate. This gradient is highly linear up to about 80% and then becomes convex. This gradient profile should therefore be considered multiphasic in that there are two distinct segments with different gradient profiles. In this case a change in flow rates was not required to produce a multiphasic gradient profile. This gradient in component B is particularly useful when transformed as shown in FIG. 16 such that the exponential rise phase 66a enters the flow cell in advance of the linear region 66b. This allows the gradient to cover a wide concentration range as is often required in affinity and kinetic assays. The transformation simply requires reversing the components where component B is placed in the mixer and component A is added to form the gradient. In addition the gradient is then injected over the sensing surface in reverse order so that the surface is exposed to component B from low concentration to high concentration.

The foregoing is an implementation of means for generating a two component liquid gradient that is preferably integral to a flow injection analysis system. A mixing compartment assures that the mixed liquid is homogenous when a first liquid is placed in the mixing compartment and a second liquid is added at a selected, known flow rate while the mixed liquid gradient is removed from the mixer at a selected, known flow rate. The volume placed in the mixing compartment and the flow rates of the second liquid stream and the mixed liquid output stream are adjusted to yield the desired gradient profile. In a particular implementation, the volume of the mixing compartment is less than 1 mL and the apparatus is situated in the sampling compartment of a fluidic autosampler. In the implementation described above, the second liquid stream and the mixed liquid output stream are provided by a dual lumen liquid probe that may be positioned in the mixing compartment and wherein each probe lumen is in fluid contact with a controlled pumping means.

Regarding the selectable flow rates, a preferred implementation of a mixer implementing the gradient generating means enables one or more of the following flow rate relationships to achieve the respective gradient(s). The mixer described above achieves this. If the flow rate of the mixed liquid output stream is equal to the flow rate of the added second liquid stream, the mixed liquid output stream has an exponential gradient of the second liquid in the first liquid. If the flow rate of the mixed liquid output stream is approximately twice the flow rate of the added second liquid stream, the mixed liquid output stream has a linearly increasing gradient of the second liquid in the first liquid. If the flow rate of the mixed liquid output stream is greater than twice the flow rate of the added second liquid stream, the mixed liquid output stream has a concave gradient of the second liquid in the first liquid. If the flow rate of the mixed liquid output stream is less than twice the flow rate of the added second liquid stream, the mixed liquid output stream has a convex gradient of the second liquid in the first liquid. If the flow rate of the mixed liquid output stream and/or the flow rate of the added second liquid stream is/are changed intermittently, the mixed liquid output stream is a complex gradient of the second liquid in the first liquid with two, or more, segments characterized by different gradient profiles.

The reference to the flow rate of the mixed liquid output stream being "approximately twice" the flow rate of the added second liquid stream is based on commercially available apparatus that provides nominal flow rates of x and 2x. The doubled (2x) flow rate only approximates linearity, whereas improved linearity can be obtained in the present invention with a flow rate relationship of 1/2.73 (input flow of the aforementioned "second liquid stream") and 1−(1/2.73) (output flow of the aforementioned "mixed liquid output stream"). This relationship is indicated above for the linear gradient of FIG. 15 (input flow rate of 37 µL/min and output flow rate of 63 µL/min). This output/input relationship of 63/37=1.7 is included in the "approximately twice" terminology used herein with regard to this aspect of the present invention. In such a particular case, greater than approximately twice can include an output flow double the input flow, for example, as indicated for the concave curve 64 of FIG. 15.

Simulation binding response curves for constant concentration and for linear, exponential and sigmoidal gradients are shown in FIG. 17. Curve 68 is a normal fixed concentration injection where the analyte concentration is 25 nanomolars (nM). Curve 70 is for the same interaction but the concentration begins at zero and grows according to a smoothly decaying exponential gradient until the final concentration approaches 25 nM. Curve 72 results from a linear concentration gradient where the concentration begins at zero and is 25 nM at the end of the injection. Curve 74 results from a sigmoidal shaped concentration gradient similar to that determined experimentally in FIG. 8.

In summary there are three approaches for how analyte gradient may be determined.

1. If the gradient is highly reproducible, then its mathematical form is a constant and once defined this may be used for all future gradient injections where no bulk index difference between sample buffer and running buffer exists. Variations in flow rate, sample volume and loop volume may be modeled and these parameters may be entered when model fitting or entered as constants. Thus, the reproducible analyte gradient can be described by a simple mathematical function and this function incorporated into a kinetic evaluation algorithm to account therein for the changing analyte concentration. This applies to all gradients produced by the gradient maker described earlier.

2. If complex gradients are prepared by any means where a defined function cannot be assumed to apply, then a bulk index gradient should be employed as described above to define that function. This procedure allows one to define a gradient function under a particular set of conditions (i.e. sample volume, loop volume, flow rate, sample loading flow rate etc). This gradient function is then applied in the kinetic/affinity model fit. Once defined this function may be assumed to apply in all future gradient injections assuming that identical conditions apply.

3. If the gradient profile is highly complex, or not accurately reproduced, then a bulk refractive index gradient should be generated with the analyte gradient. Usually it is recommended that the bulk refractive index of the sample and that of the running buffer be matched as closely as possible to avoid complications in fitting models. However, these complications are not significant as long as the bulk index change is not extremely high. For example it is possible to simply ensure that the bulk refractive index of the sample buffer is slightly higher (e.g. ~100 RU which is equivalent to 100 µrefractive index units) than that of the running buffer. Then when the gradient is injected, the gradient profile is present in the reference channel response (assuming low non-specific binding) and the response in the active sensing channel (coated with ligand) will be the product of both the binding interaction and the bulk refractive index gradient. The binding response is determined by subtracting the reference response from the active channel response. The gradient profile is determined from the reference channel, and this is used to estimate the changing concentration of analyte during the injection. A 4-parameter logistic expression as discussed earlier may be appropriate. Other non-linear models may be fitted, including complex polynomials. If a suitable expression that accurately fits to the gradient profile cannot be found, then it is possible to simply use the gradient itself. For example, add sucrose to a final concentration of 0.13% weight per weight (w/w) to the analyte sample (i.e. component B). A solution containing 0.13% (w/w) sucrose will give a bulk refractive index response of 100 RU. Prepare a complex gradient giving a complex profile as shown in FIG. 18. If the gradient is prepared such that it is allowed to approach the maximum concentration of sucrose, then the maximum expected response will be 100 RU. At that time it is assumed that the concentration of component B (i.e. analyte) will also be 100%. Therefore the gradient can be normalized by dividing by the expected maximum bulk refractive index response to give the unit gradient profile (i.e. fraction of component B present) as a function of time as shown in FIG. 19. The concentration of analyte at time t is then obtained by multiplying the maximum analyte concentration (i.e. analyte concentration in component B) by the corresponding fraction at that time point. Interpolation between the points may be optionally employed. Thus, in such case the method of the present invention can include binding analyte with analyte binding species on a first sensing surface of the flow cell, thereby forming binding reactions, and continuing to flow the analyte concentration gradient over a second sensing surface of the flow cell, wherein the second sensing surface does not include analyte binding species; empirically determining a profile of the analyte gradient, including creating a bulk refractive index difference between the sample liquid and the second liquid and detecting a reference response to the bulk refractive index difference from the response of the second sensing surface to the flow of analyte concentration gradient thereon, wherein the reference response includes a gradient in bulk refractive index; recording the gradient in bulk refractive index as the analyte gradient; and incorporating the gradient in bulk refractive index as analyte gradient in at least one kinetic evaluation algorithm in order to account for the changing analyte concentration.

The present invention also encompasses use with samples having more than one analyte. Most simply, there can be one analyte fluid within another fluid having a different analyte, one of which fluids can be referred to as the carrier fluid. Such other fluid contains unbound analyte binding species such that mixing the two fluids forms a dual gradient wherein the concentration of the analyte and the concentration of the unbound analyte binding species both form continuous gradients. For example, if these gradients are for two molecules (A and B) that possess affinity towards each other, the ratio of the two reactants at any point in the gradient will change. Once created, the two-component gradient may be injected. If the gradient is injected immediately, then the resulting interaction curve will possess kinetic information and may be analyzed using the competitive kinetic model derived by Motulsky and Mahan (see "The Kinetics of Competitive Radioligand Binding Predicted by the Law of Mass Action," Molecular Pharmacology, 25:1-9 (1983)), later modified by Karlsson (see "Real-Time Competitive Kinetic Analysis of Interactions between Low-Molecular-Weight Ligands in Solution and Surface-Immobilized Receptors," Analytical Biochemistry 221: 142-151 (1994)), and further modified by Nieba, Krebber, and Pluckthun (see "Competition BIAcore for Measuring True Affinities: Large Differences from Values Determined from binding Kinetics," Analytical Biochemistry 234: 155-165 (1996)). These models return the association rate constant and the dissociation rate constant. If the gradient components are allowed to form steady state complexes before being injected, then the resulting binding curve may be interrogated to yield the affinity constant for the interaction.
More Applications of Biomolecular Interaction Analysis (BIA) using Analyte Gradients.
Competitive Solution Phase Affinity A competitive two component gradient of the solution phase affinity model can be analyzed rapidly by analyzing the change in the observed binding rate in the presence of a competitor/inhibitor. The Nieba et al. reference cited above reported a competitive affinity approach based on the determination of the observed rate constant for a series of conventional binding interaction curves where the analyte is mixed with different concentrations of free ligand (or competitor). This model is based on the aforementioned models of Karlsson and Motulsky/Mahan. In the Nieba et al. method the two component gradient is allowed to reach equilibrium before being injected. The differential equations of the simple 1:1 interaction model were described above. Here is the main differential equation where the rate of change of complex formation is described:

$$dAB/dt = (ka*A*B - kd*AB)$$

where A=analyte concentration
B=ligand concentration
ka=association rate constant
kd=dissociation rate constant
AB=complexes formed from A+B
A biosensor measures complex formation so that AB formation is the biosensor response, R. The integrated form of the differential equation for the association phase is therefore $$R_t = (r_o/k_{obs})(1 - e^{(-k_{obs}t)})$$

where $r_o = ka*A*Rmax$
Rmax is the maximum analyte binding response at saturation
$k_{obs}$ is the observed rate constant $= ka*A + kd$ In this model inhibition of binding to surface bound ligand because of the presence of a competitor in the sample causes a reduction in the observed rate constant ($k_{obs}$). This may be compared to the observed rate constant recorded for the same analyte concentration when the competitor is absent ($k_{obs0}$). An embodiment of the present invention adapts this model to account for a gradient in the concentration of inhibitor as the injection proceeds. When the model is adapted to account for an inhibitor gradient, there is sufficient information in a single gradient curve to estimate $k_{obs0}$ along with the KD. This enables the affinity constant to be determined from a single binding response curve. This is in contrast with U.S. Pat. No. 5,753,518 to Karlsson and U.S. Pat. No. 6,143,574 to Karlsson et al. The present invention disclosed herein allows the KD for the inhibitor-analyte interaction to be determined as well as $k_{obs0}$ for the analyte-ligand interaction, all from a two component gradient binding response curve. Furthermore the dissociation phase of this gradient interaction curve may be used to determine the dissociation rate constant (kd) for the analyte-ligand interaction. It is also presently contemplated that since both $k_{obs0}$ and kd are known, then the association rate constant (ka) for the analyte-ligand interaction can be calculated from the following: $ka = (k_{obs0} - kd)/A$. Thus the modified model may be fitted to a single response curve for a two component gradient in order to return the solid phase kinetic constants for the analyte-ligand interaction and the solution phase affinity constant for the inhibitor-analyte interaction. If the inhibitor is not a different species but is simply more ligand molecules present in the bulk solution, then this method provides a convenient self consistency check where the KD calculated from the ratio of the solid phase kinetic constants should approximate the solution phase steady state KD. Therefore the two component gradient injection method that is an object of the present invention provides a fast information rich method for determining kinetic and affinity constants and without regeneration. This information cannot be obtained from a single binding interaction curve using non-gradient methods.

In the example below a linear gradient in the inhibitor concentration is assumed.

$$Increment = I/Inject\ Time,$$

where I is the maximum inhibitor concentration
Inject Time is the duration of the injection in seconds
Increment is the change in inhibitor concentration each second.

$$Is = Increment*t$$

where Is the concentration of inhibitor at any time, t $$W = (B0 + Is + KD)/2$$

where B0 is the free ligand concentration
KD is the affinity constant for the inhibitor The change in the observed rate constant as a result of inhibition is then given by the following $$k_{obs}=(k_{obs0}/B0)*(B0-W+((W^2)-Is*B0)^{0.5})$$

where $k_{obs0}$ is the observed rate constant in the absence of the inhibitor.

Then the association phase of the binding response curve is fitted with the following expression for the association phase with respect to time (t):

$$\text{Association}=\text{BASELINE}+(r_0/k_{obs})*(1-e^{(-1*k_{obs}*t)})$$

Optionally the dissociation phase may be used to confirm the kd for the analyte interaction with immobilized ligand. Thus the dissociation phase is described as follows:

$$Y\text{atSTOP}=(r_0/k_{obs})*(1-e^{(-1*k_{obs}*\text{Inject Time})})$$

$$\text{Dissociation}=Y\text{atSTOP}*e^{(-1*kd*(t-\text{Inject Time}))}$$

Simulation

Using the above model a simulation yields an expected curve where each parameter is given typical values that might be expected experimentally. In the following simulation $$I=1.000000*10^{-8}\text{ M}$$

$$B0=1.000000*10^{-8}\text{ M}$$

$$KD=1.000000*10^{-7}\text{ M}$$

$$k_{obs0}=0.01\text{ s}$$

$$\text{BASELINE}=0.0\text{ RU}$$

$$r_0=1.0$$

$$kd=0.001\text{ s}^{-1}$$

Both the association phase and dissociation phase were 300 seconds. The resulting response of the simulation is shown in FIG. 20. In contrast to Nieba et al., simulations using the present model described above show that an experimentally determined $k_{obs0}$ where no inhibitor is present is not required. In the embodiment of the invention disclosed here experimental determination of $k_{obs0}$ is optional. Since I and B are known, then KD and $k_{obs0}$ are the only fitted parameters when fitting this model to a real curve. In the simulated data set shown in FIG. 20 the model was fitted (curve 76) to the simulated curve (curve 78) where KD and $k_{obs0}$ were fitted as unknowns and the correct values were successfully returned. Therefore the present invention includes this single injection gradient method wherein the KD may be determined from a single injection.

Competitive Kinetic Model

A competitive kinetic model was derived and applied as described by the previously cited references from Motulsky and Mahan and from Karlsson. In this model a competition between two analyte species for immobilized ligand binding sites results in complex binding interaction curves. The interactants are mixed just prior to analysis. A particular advantage of this method is that one of the analyte species may possess a very low molecular weight (i.e. designated the inhibitor) and therefore give rise to very low (even undetectable) binding responses yet its kinetic binding constants when interacting with the immobilized ligand may still be determined from the resulting inhibition of the large analyte binding response. This is similar to the competitive affinity approaches discussed above but allows kinetic constants to be determined. Therefore it is not necessary to wait for steady state to develop in order to extract kinetic constants from the data. The model as applied by Karlsson, cited above, requires multiple binding response curves representing multiple different inhibitor concentrations in the presence of a fixed concentration of analyte. The curves are then fitted with the model that returns the kinetic constants for the inhibitor-ligand interaction. The kinetic constants for the interaction of the large analyte with immobilized ligand are best predetermined and then fitted as constants thereby improving the reliability of the inhibitor kinetic constants as estimated from the model.

A preferred embodiment of the present invention includes an adaptation of the Motulsky and Mahan and Karlsson competitive kinetic models to the gradient injection method of the present invention such that a single competitive binding interaction curve possesses enough kinetic information to enable the kinetics of the interaction of inhibitor with analyte in solution to be determined from a single binding interaction curve. This again avoids the need to regenerate the surface.

The new model of the present invention assumes that the inhibitor is a low molecular weight molecule that gives rise to a negligible binding response and it is therefore assumed not to contribute to the binding response. However, if its mass is significant, then the model may be adjusted to account for this as described by Karlsson in the previously cited reference.

$$\text{Increment}=I/\text{Inject Time},$$

where I is the maximum inhibitor concentration
Inject Time is the duration of the injection in seconds
Increment is the change in inhibitor concentration each second.

$$Ig=\text{Incremenet}$$

where Ig is the concentration of inhibitor at any time, t
The equation is complicated so it is best written by designating terms, namely four terms (KA, KB, KF and KS) in the notation used by Motulsky et al. in their paper cited above. These are not to be confused with affinity and kinetic constants.

$$KA=ka*A+kd$$

$$KB=ka'*Ig+kd'$$

where ka' and kd' are the kinetic constants for the inhibitor-ligand interaction.

$$S=\text{SQRT}((KA-KB)^2+4*ka*kd*A*Ig)$$

$$KF=0.5*(KA+KB+S)$$

$$KS=0.5*(KA+KB-S)$$

$$\text{DIFF}=KF-KS$$

$$Q=B\max*ka*A/\text{DIFF}$$

Then the association phase of a gradient injection as a function of time is described by the following equation:

$$\text{ASSOCIATION}=Q*(k4*\text{DIFF}/(KF*KS)+((kd'-KF)/KF)*e^{(-KF*t)}-((k4-KS)/KS)*e^{(-KS*t)}),$$

where k4 is kd of the second interaction.

Simulation

Using the above model produced the following simulated expected binding response curve. The dissociation phase was omitted as this portion of the binding interaction curve is not required by the model. The following constants were employed.

$$ka=1000000.0\text{ M}^{-1}\text{s}^{-1}$$

$$A=5.0*10^{-8}\text{ M}$$

$$kd=0.001\text{ s}^{-1}$$

$ka' = 1000000.0 \text{ M}^{-1}\text{s}^{-1}$ $I = 1.0*10^{-8} \text{ M}$ $kd' = 0.001 \text{ s}^{-1}$ $B\text{max} = 100.0 \text{ RU}$ Referring to FIG. 21 the simulation-obtained curve 80 is shown fitted with the model curve 82 where ka' and kd' are fitted as unknown parameters. The model successfully returned the correct kinetic values. Therefore it is expected that a single binding association phase curve is sufficient to obtain the kinetic constants for the interaction of the inhibitor with the ligand. Although not essential the kinetic constants for the analyte interaction (i.e. ka and kd) should be predetermined and entered as constants in the model. In some cases the inhibitor may in fact be the same molecule as the immobilized ligand. In this case this free ligand behaves as an inhibitor. The model can therefore be simplified to a single set of kinetic constants. If separate kinetic constants are retained for such a free ligand inhibitor, then it is possible to determine any variations in solution phase and solid phase kinetics in a single binding interaction curve. In common with the other gradient methods this method also allows one to avoid surface regeneration. The complex shape of the gradient inhibition curve is information rich allowing a single curve to replace a set of curves covering a range of inhibitor concentrations.

pH Gradient for Controlled Immobilization (i.e. Controlled Pre-concentration)

When approaching the kinetic analysis of an unknown affinity interaction, it is useful to perform several pilot experiments prior to kinetic analysis. In many cases the isoelectric point of these interactants will be unknown. The isoelectric point (pI) is the pH at which the net charge of the biomolecule is zero. Electrostatic charge pre-concentration of the ligand onto the surface is usually necessary for ligand immobilization and this requires that the ligand be positively charged. The ligand is usually made positively charged by dissolving it in a low pH buffer. Pre-concentration of the positively charged ligand occurs when it is exposed to an electronegative sensing surface. The total salt concentration must be low in order to prevent neutralization of the electrostatic fields. However, the preferred covalent coupling reaction (i.e. amine coupling via surface bound N-hydroxysuccinimide esters) proceeds best at neutral pH. Therefore the optimum pH is the closest to neutral pH at which pre-concentration of the ligand becomes effective. This pH is usually determined empirically by a series of injections. To determine the optimum pH it is necessary to prepare the ligand in a series of buffers where the pH varies. For example a series of fifteen samples covering a range of three pH units at increments of 0.2 pH units, may be injected. Samples are preferably injected from high pH to low pH. This process is usually terminated once an injection that yields adequate pre-concentration is recorded. This is a time consuming process and also consumes valuable reagents.

This process is greatly accelerated by using a gradient injection of the present invention that covers the pH range of interest. In this way the optimum pH is determined from a single injection that can be performed in a few minutes. For example—(1) sample is prepared at 10 micrograms per milliliter (μg/mL) in 10 millimolar (mM) sodium acetate buffer, pH 5.5; (2) sample is also prepared at 10 μg/mL in 10 mM sodium acetate buffer, pH 3.8; and (3) a linear gradient of the low pH sample is prepared against the high pH sample. The pH varies along the gradient. The gradient is preferably injected from high to low pH. An increase in the response is observed when the pH of the injected gradient passes the pI of the ligand. This point identifies the pH threshold at which pre-concentration begins. The ratio of the two buffer solutions is known at all points during the gradient and hence the expected pH at each point is easily calculated. It may be desirable to decrease the pH below this threshold pH if a large pre-concentration effect is desirable (e.g. if a large amount of ligand is to be immobilized). However in many cases a small amount of ligand must be immobilized and in this case it is not necessary to lower the pH much further.

Such pH gradients may be composed of any mixture of acid and base solutions and the pH of such solutions may be calculated from the conventional equations from acid-base equilibrium. The ideal pH is defined more precisely because this pH gradient injection method provides the scientist with higher quality data with higher resolution and in a fraction of the time. This is particularly important in cases where only a very narrow pH range exists over which a ligand can be successfully immobilized. This is often the case with acidic ligand.

Regeneration/Complex Stability Gradients

Once an analyte binds to immobilized ligand it must be removed in order to restore the analyte binding capacity before proceeding to the next analyte sample. This removal of affinity captured material is referred to as regeneration and it is one of the most difficult aspects of real-time BIA. In many cases the affinity complexes are very strongly bound to one another necessitating the use of harsh regeneration solutions. These solutions dissociate the affinity complexes by creating unfavorable conditions that overcome the binding interaction forces. Acids and bases are usually effective but other aqueous solution containing quantities of chaotrophic agents such as non-aqueous solvents, guanidine-HCl and urea are also employed. The list of reagents and reagent mixtures that have been successfully used is extensive. Usually optimization of regeneration requires a trial and error approach where multiple solutions are evaluated. In many cases this process may require days if not weeks to optimize. In some cases finding an effective regeneration solution that maintains the analyte binding capacity is not possible. The aforementioned process may be accelerated according to the present invention by replacing multiple injections of different reagents with a reagent gradient.

For example phosphoric acid is often successfully applied to regenerate interactions but the effective concentration varies greatly from one interaction to the next. The goal is to use the lowest concentration in order to limit damage to the immobilized ligand due to denaturation. In the interest of saving time many researchers are tempted to reduce the number of samples to be evaluated. This unfortunately has a negative impact on method development. So with the present invention a single injection with a varying gradient is used. As an example with the present gradient method, the gradient varies from pure water to 100% 0.1 M phosphoric acid. This gradient is then injected from low concentration to high concentration over an analyte-coated sensing surface. The gradient concentration at which the analyte-ligand complexes start to dissociate is identified as the point during the gradient injection when the response begins to decrease due to dissociation. The actual concentration of phosphoric acid at this point may then be calculated. This represents the threshold concentration at which regeneration becomes effective. However the gradient may be allowed to proceed until full regeneration of the surface occurs. Full regeneration of the surface is observed as a plateau in the response where no further decrease in response is observed. In addition the total response drop during the gradient injection should approximately equal the analyte binding response preceding the regeneration experiment. An ideal response curve is shown in FIG. 22. These regeneration gradients may be composed of mixtures of two or more reagents and may possess any gradient form. In most cases a linear gradient is suitable.

In addition to determining regeneration conditions such reagent gradients can be used to investigate the stability of affinity complexes to various environmental conditions. For example it may be of interest to determine the complex stability on exposure to a solution containing increasing concentrations of salt (e.g. sodium chloride). A salt gradient could be prepared over any desired range, for example 10 mM NaCl to 1 M NaCl. Ideally the pH of the solution would be held constant by using 10 mM buffered salts as the lowest salt concentration. As before, the gradient is injected over an analyte coated surface and the response recorded. In this case a large bulk refractive index change is also measurable during the gradient injection requiring reference curve subtraction from an uncoated sensing surface. The effect of changing the concentration of any reagent, or mixture of reagents, on preformed affinity complexes may be determined more rapidly using a gradient as opposed to running a large number of multiple sequential injections. Various known reagents can be considered for such studies. Furthermore the effect of reagents on the formation of affinity complexes may similarly be tested by creating an analyte injection containing a gradient in some additive. Ideally the analyte concentration would be held constant.

Analyte Gradient for Concentration Range Finder

After a ligand has been successfully immobilized it is necessary to inject analyte over the surface to confirm binding activity. If the approximate affinity for the interaction is unknown then a micromolar concentration of analyte is usually recommended for the first analyte injection. This ensures that medium affinity binding interactions are detectable thereby eliminating any false negative test. Unfortunately in some cases the surface is saturated so fast that the association phase curve does not possess enough information to determine an association rate. It is still possible to determine a dissociation rate constant by allowing the complexes to dissociate by at least 5% before regenerating the surface. However, if in practice the actual affinity of the interaction is very high, then regeneration of the surface may be very difficult and optimization of regeneration would be required. Usually the interaction surface is damaged by this process and it is common to consume several sensors before optimization experiments are complete. It is desirable to obtain an estimate of the affinity and/or kinetic parameters before regeneration experiments are required. This can be accomplished by exploiting an analyte gradient injection.

A gradient beginning with zero analyte and rising to micromolar concentrations of analyte is prepared. The gradient is injected over a ligand-coated surface from low concentration to high concentration. A gradient profile with an exponential increase in concentration is ideal but other gradient profiles could be used. The threshold concentration at which binding of analyte becomes detectable is then identified as an increase in the response that is at least three times the standard deviation of the baseline noise after reference curve subtraction. A binding response of 1-2 RU is usually significant. The binding capacity of the surface when saturated with analyte normally exceeds 50 RU. The injection may be optionally terminated thereby preventing the surface from being saturated. Since only 2-4% of the surface capacity is consumed by this test it is possible to proceed with the next analyte injection without regeneration. However, this "concentration range finder" experiment identifies the concentration at which the analyte binding response becomes detectable and that is easily related to an approximate affinity. In a preferred embodiment a 1:1 kinetic model with a mass transport limitation term is fitted to obtain a rough estimate of the on and off rates. With this information it is trivial to estimate the analyte concentration required to saturate the surface in reasonable time. Usually an analyte concentration that is capable of saturating the surface after a two minute contact time is suitable for kinetic analysis as its association phase possesses sufficient information for a reasonable approximation of the "true" association rate constant as determined from a full set of kinetic binding curves covering a wide range of concentrations. Alternatively this information can be used to determine the upper concentration limit of an analyte gradient injection. In a preferred embodiment the shape of the analyte gradient is chosen such that the "range finder" test covers a concentration range spanning a few orders of magnitude. A gradient injection spanning an exponentially increasing analyte concentration from picomolar (pM) to high micromolar ($\mu$M) covers the vast majority of possible affinity ranges and would contain sufficient information to provide a full kinetic analysis of the interaction without regeneration. The gradient of FIG. 16 is ideal for this application as it is characterized by a slow exponential rise phase followed by a linear phase. This gradient profile maximizes the information content of the resulting binding interaction curve.

The various composition gradients referred to herein can be formed by any suitable means, including those described in this specification.

The references cited above are incorporated herein by reference.

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by claims when they are appended.

What is claimed is:

1. A method for determining an affinity or kinetic constant for ligand binding comprising the steps of:
   creating a gradient sample by mixing a first gradient component solution comprising an analyte having a starting concentration with a second gradient component solution in a channel connected to an inlet of a flow cell such that an analyte concentration gradient is generated thereby providing a range of analyte concentrations within the gradient sample;
   injecting, in a single, continuous injection, the gradient sample into the flow cell and onto a first sensing surface and a second sensing surface, wherein the first sensing surface comprises a ligand immobilized thereon and the second sensing surface is free of immobilized ligand;
   adding to one of the gradient component solutions a material that changes the bulk refractive index thereof;
   recording a first response at the first sensing surface and a second response at the second sensing surface, wherein the first response includes a binding response component elicited by an interaction between the analyte and the ligand thereby providing a binding response curve, and wherein the second response provides an actual bulk refractive index response of the gradient sample;
   determining a gradient injection profile based on the second response;

extrapolating the range of analyte concentrations present at the first sensing surface by performing the following steps:

generating an adjusted bulk refractive index response by dividing the actual bulk refractive index response by a maximum expected bulk refractive index response for a 100% pure solution of the material that changes the bulk refractive index;

fitting an equation to the adjusted bulk refractive index response using a regression curve fitting procedure that suitably models the gradient injection profile of the gradient sample as a function of injection time thereby defining a gradient injection profile function;

multiplying the starting concentration of the analyte by the gradient injection profile function in order to estimate the range of analyte concentrations at the first sensing surface as a function of time during the gradient injection;

using the extrapolated range of analyte concentrations for determining at least one of a plurality of kinetic or affinity constants for the binding response component.

2. The method of any one of claim 1 wherein the material that changes the bulk refractive index is selected from the group comprising sugars, polysaccharides, glycols, hydrogels, salts, hydrophilic polymers and water miscible solvents.

3. The method of claim 1 wherein the first response further comprises a bulk refractive index component such that individual response contributions of the binding response component and the bulk refractive index component are resolved from the binding response curve as a function of injection time by employing non-linear regression curve fitting of predefined mathematical models.

* * * * *